United States Patent
Hannani et al.

(10) Patent No.: US 8,491,585 B2
(45) Date of Patent: Jul. 23, 2013

(54) METHODS AND SYSTEMS FOR MINIMALLY INVASIVE LATERAL DECOMPRESSION

(76) Inventors: Kambiz Hannani, West Covina, CA (US); Frank Litvack, Los Angeles, CA (US)

(*) Notice: Subject to any disclaimer, the term of this patent is extended or adjusted under 35 U.S.C. 154(b) by 339 days.

(21) Appl. No.: 12/772,883

(22) Filed: May 3, 2010

(65) Prior Publication Data
US 2010/0286695 A1 Nov. 11, 2010

Related U.S. Application Data

(60) Provisional application No. 61/176,010, filed on May 6, 2009.

(51) Int. Cl.
*A61B 17/00* (2006.01)

(52) U.S. Cl.
USPC .................................................. 606/80

(58) Field of Classification Search
USPC ..................................... 606/79–85, 99, 104
See application file for complete search history.

(56) References Cited

U.S. PATENT DOCUMENTS

| | | | |
|---|---|---|---|
| 5,123,403 A | 6/1992 | Lavyne | |
| 5,755,718 A | 5/1998 | Sklar | |
| 5,803,904 A | 9/1998 | Mehdizadeh | |
| 5,961,522 A | 10/1999 | Mehdizadeh | |
| 6,096,042 A | 8/2000 | Herbert | |
| 6,174,313 B1 | 1/2001 | Bonutti | |
| 6,258,093 B1 | 7/2001 | Edwards et al. | |
| 6,740,090 B1 | 5/2004 | Cragg et al. | |
| 7,553,307 B2* | 6/2009 | Bleich et al. | 606/1 |
| 7,555,343 B2* | 6/2009 | Bleich | 607/43 |
| 7,738,968 B2* | 6/2010 | Bleich | 607/117 |
| 2005/0165405 A1 | 7/2005 | Tsou | |
| 2005/0197661 A1* | 9/2005 | Carrison et al. | 606/79 |
| 2005/0203533 A1 | 9/2005 | Ferguson et al. | |
| 2006/0004369 A1* | 1/2006 | Patel et al. | 606/79 |
| 2006/0217728 A1 | 9/2006 | Chervitz et al. | |
| 2006/0241648 A1* | 10/2006 | Bleich et al. | 606/103 |
| 2007/0270865 A1* | 11/2007 | Arnin et al. | 606/80 |
| 2008/0071282 A1 | 3/2008 | Assell et al. | |
| 2008/0221383 A1 | 9/2008 | Way et al. | |
| 2009/0036936 A1 | 2/2009 | Solsberg et al. | |
| 2009/0076511 A1 | 3/2009 | Osman | |
| 2009/0088848 A1 | 4/2009 | Martz et al. | |
| 2009/0177241 A1* | 7/2009 | Bleich et al. | 606/86 R |

OTHER PUBLICATIONS

International Search Report and Written Opinion of PCT Application No. PCT/US2010/033756, mailed Jun. 30, 2010.

* cited by examiner

*Primary Examiner* — Kevin T Truong
*Assistant Examiner* — David Bates
(74) *Attorney, Agent, or Firm* — Wilson, Sonsini, Goodrich & Rosati

(57) ABSTRACT

A system for laterally decompressing one or more spinal nerves comprises an access sheath, a tool guide, and a bone removal tool. The access sheath is percutaneously placed adjacent a facet joint using needle dilation or a small incision. The tool guide is then placed through the access sheath adjacent an anterior surface of the superior articular process of the facet joint. The bone removal tool is advanced over the guide track to remove bone from the anterior surface. Optionally, after bone removal has been completed, the cutting tool may be advanced through the access sheath in order to partially cut the ligamentum flavum to further relieve compression of the spinal nerve(s).

24 Claims, 17 Drawing Sheets

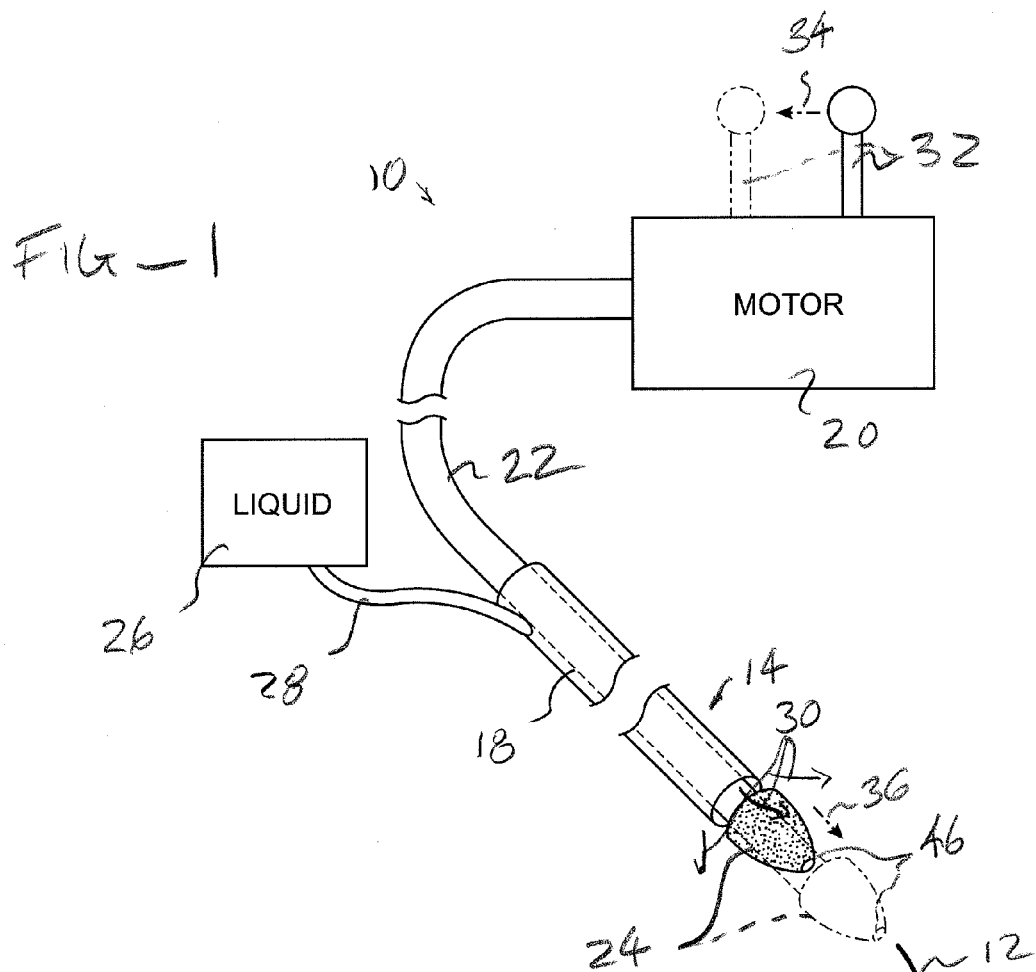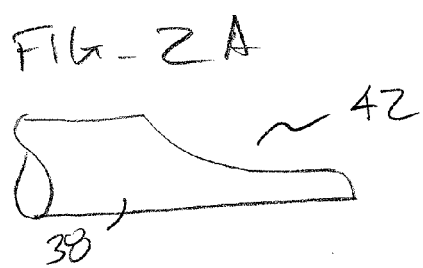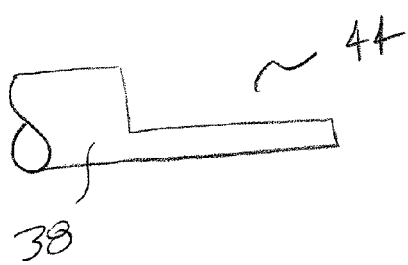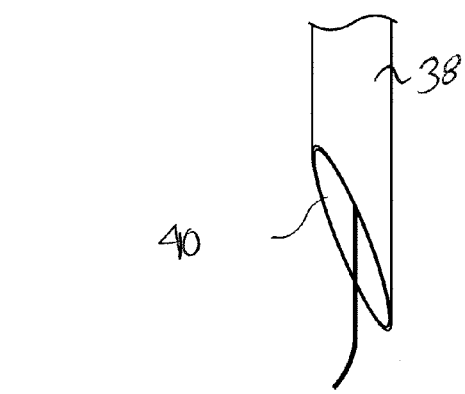

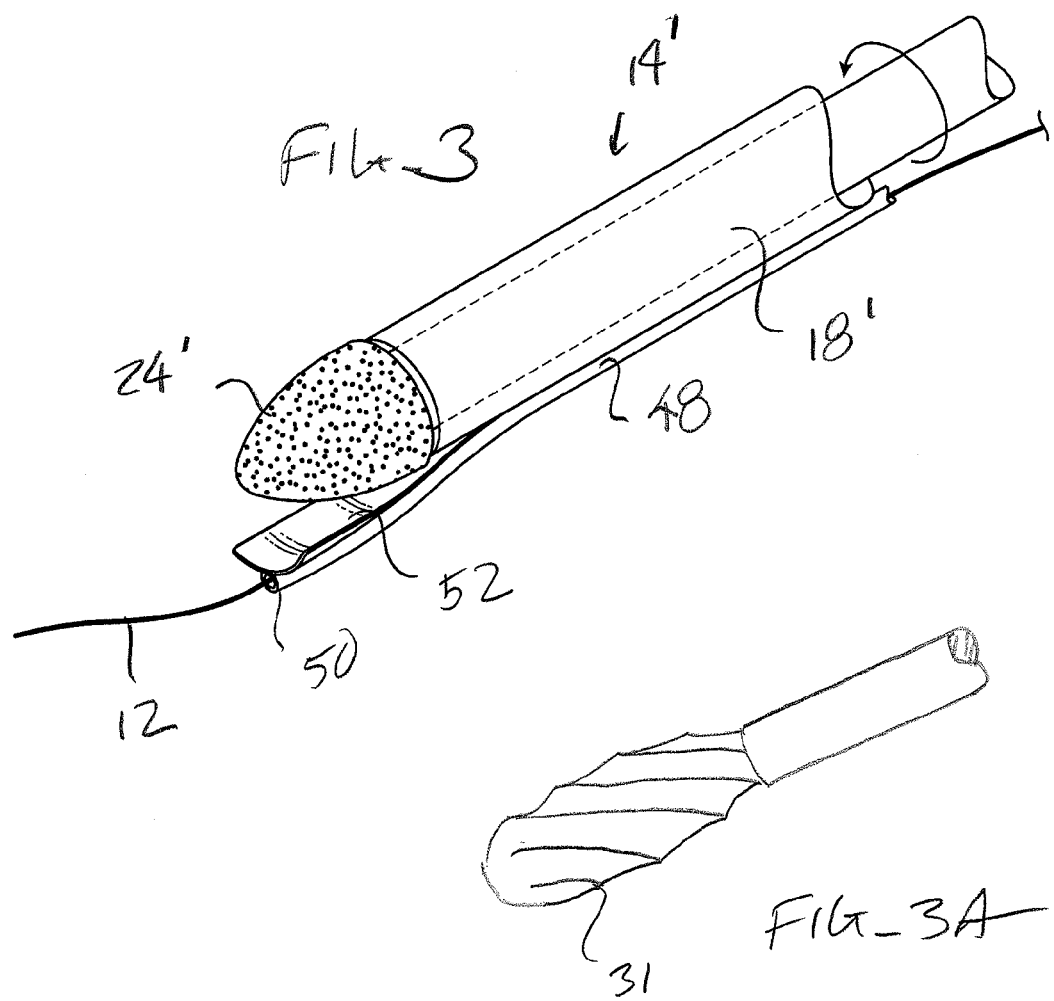

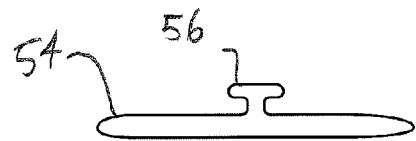
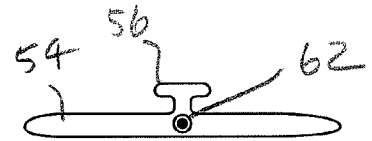
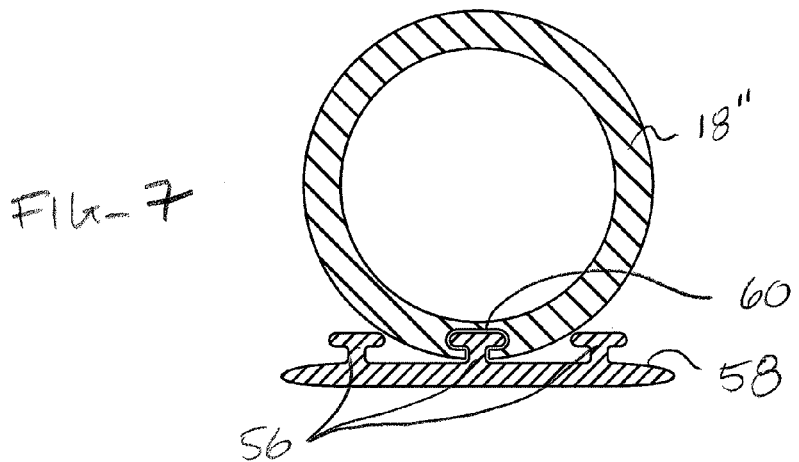
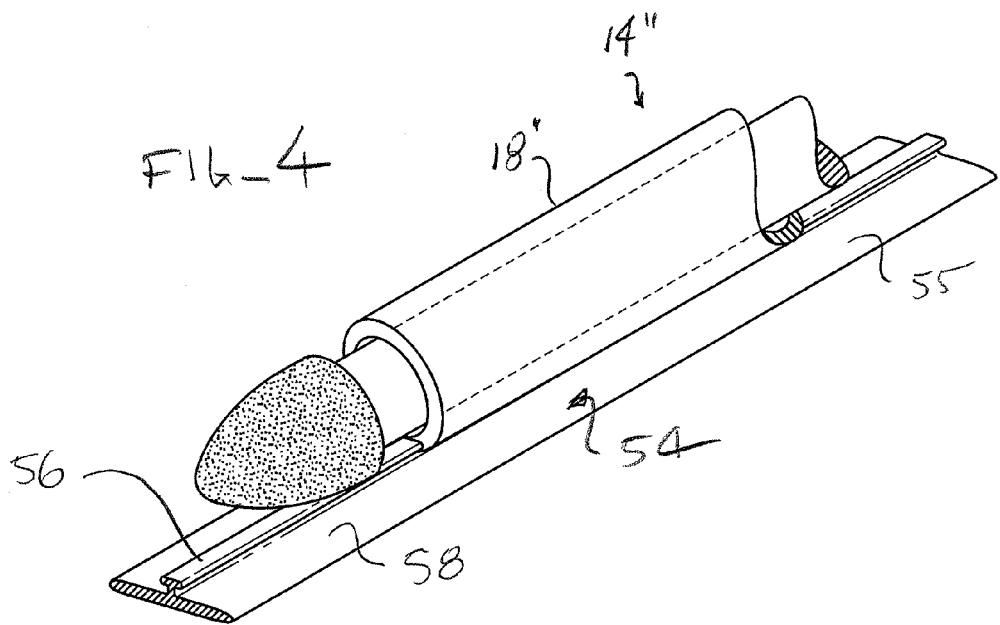

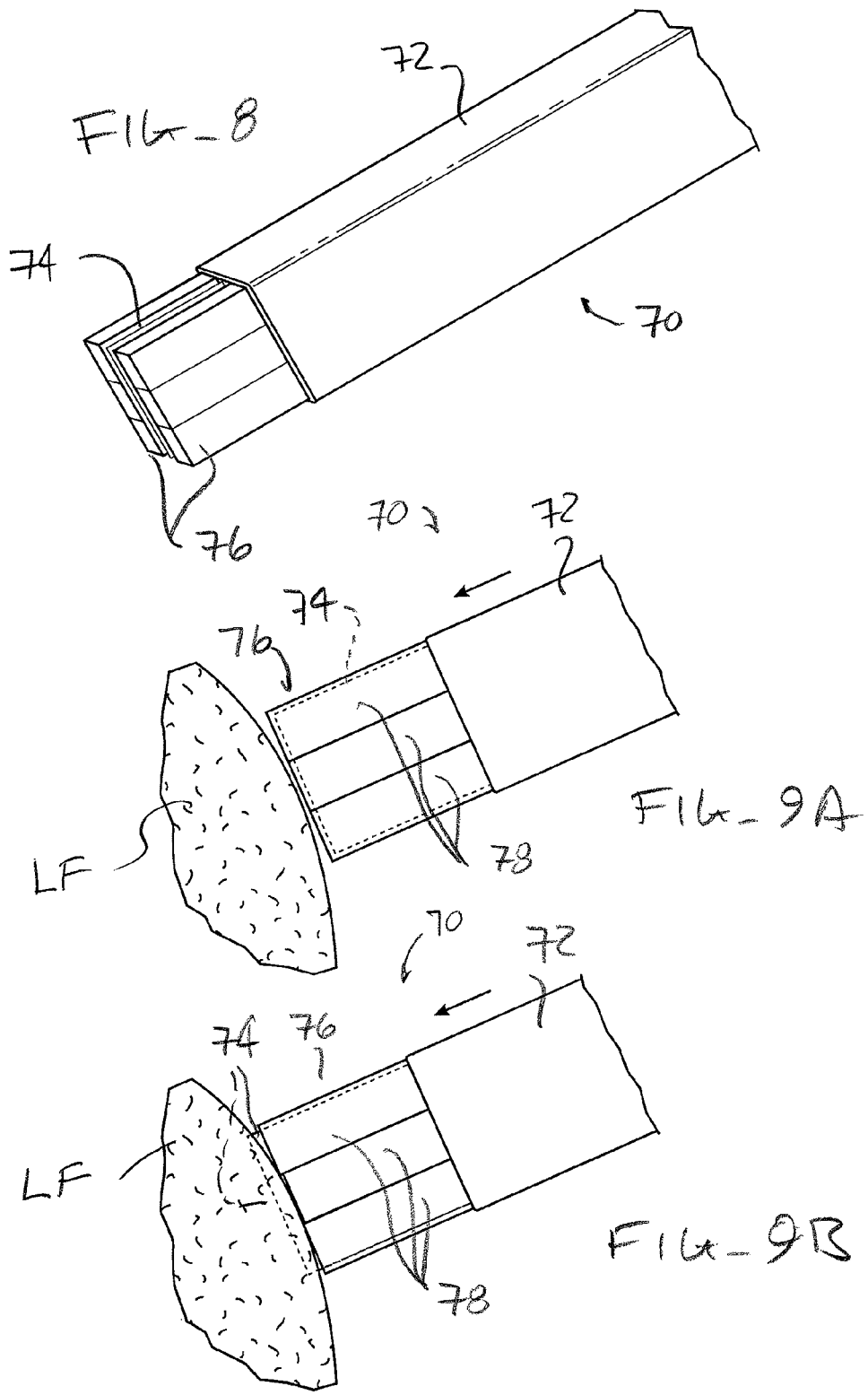

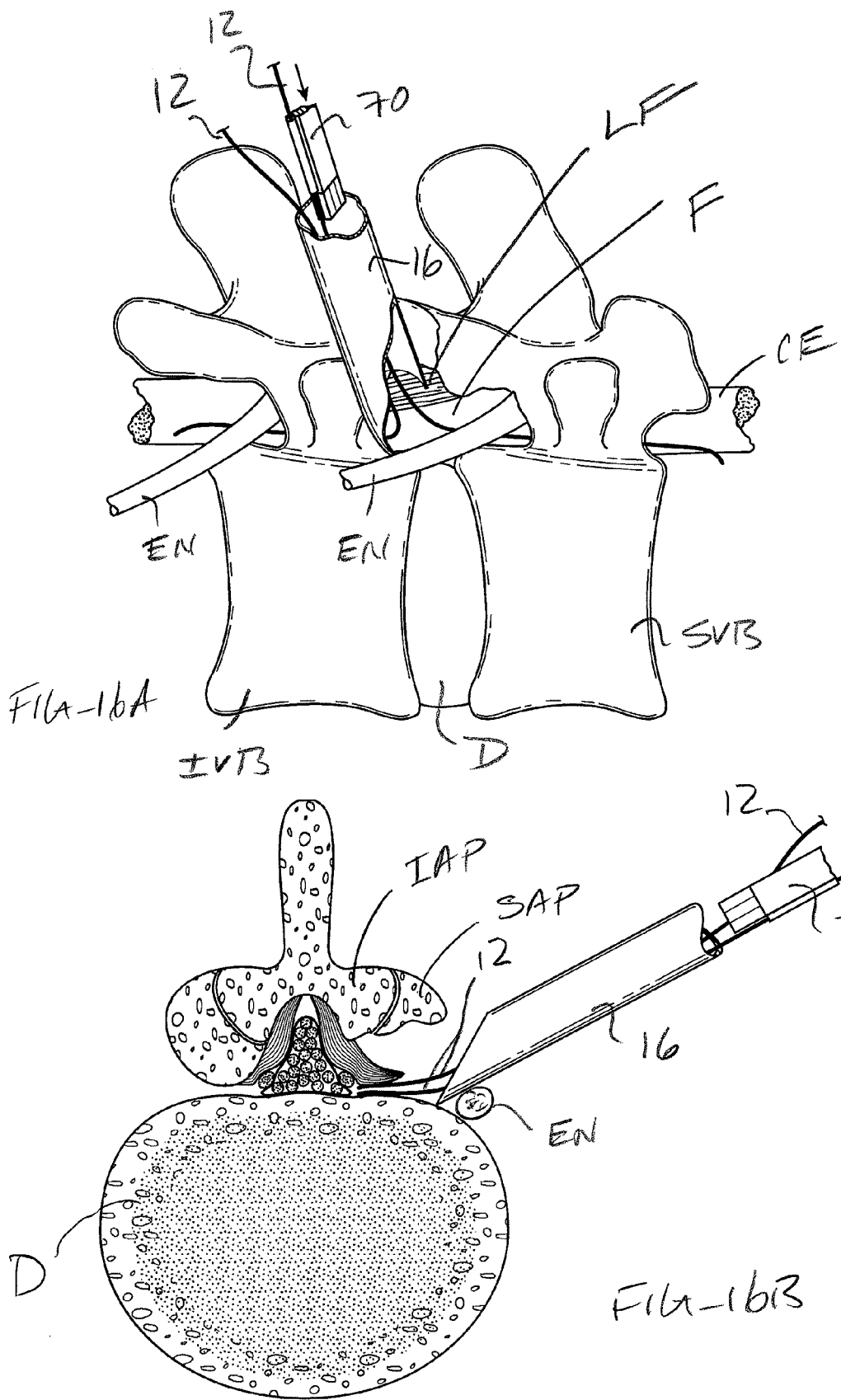

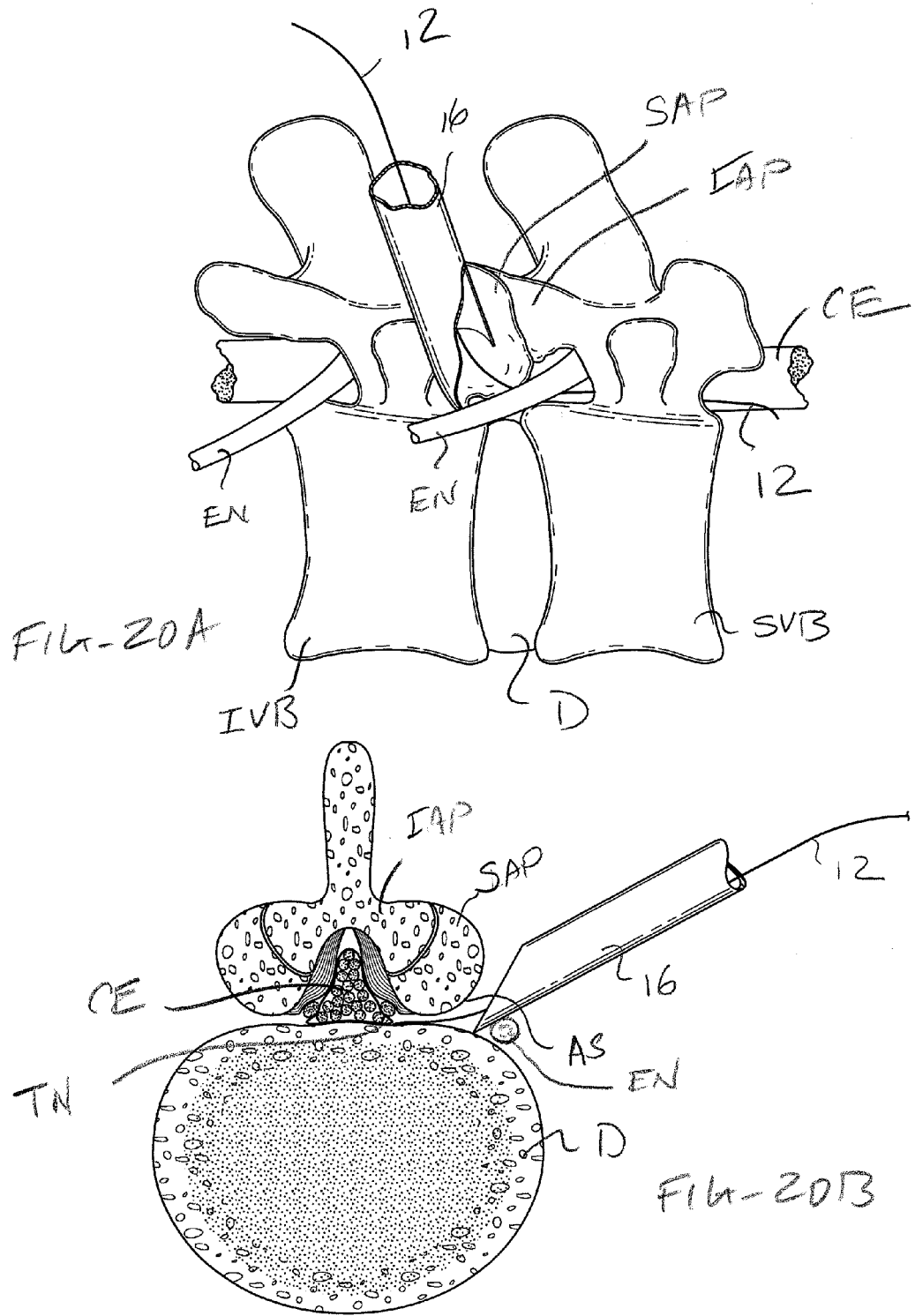

METHODS AND SYSTEMS FOR MINIMALLY INVASIVE LATERAL DECOMPRESSION

CROSS-REFERENCES TO RELATED APPLICATIONS

This application claims the benefit of provisional application No. 61/176,010 filed on May 6, 2009, the full disclosure of which is incorporated herein by reference.

BACKGROUND OF THE INVENTION

1. Field of the Invention

The present invention relates generally to medical methods and devices. More particularly, the present invention relates to methods and apparatus for laterally decompressing spinal nerves to relieve lower back and/or leg pain.

Spinal diseases are among the most frequent causes of discomfort and disability in patients in the United States and elsewhere around the world, frequently requiring surgical intervention for relief. Back and/or leg pain resulting from spinal disease is frequently the result of spinal stenosis which result from narrowing of one or more nerve passages in the spine, most often in the upper (cervical) spine or the lower (lumbar) spine. Such narrowing can apply pressure to the spinal nerves which can cause a variety of symptoms, including pain, cramping, numbness in the legs, back, neck, shoulders, or arms. In some cases, there will be a loss of sensation and/or motor function in the arms or legs and in other cases, bladder or bowel function can be adversely impacted.

Of particular interest to the present invention, pain in the lower back and legs often arises from spinal stenosis in the lumbar spine when the spinal canal or foramen (the area where nerve roots exit the spinal canal) is stenosed applying pressure to a spinal nerve, such as a transversing nerve, an exiting nerve, or nerves of the cauda equina.

While mild symptoms of spinal stenosis in the lumbar region and elsewhere can frequently be treated with pain relievers, physical therapy, braces, or other non-surgical approaches, more severe cases frequently require surgical intervention. Conventional surgical interventions include laminotomy and medial facetectomy, where small portions of the lamina and superior articular process are removed to relieve pressure on the traversing nerve roots. Foraminotomy is an alternative procedure which removes a small portion of the superior articular process and lamina to enlarge the space surrounding the exiting nerve roots.

While often effective, each of these treatment protocols generally requires surgical access to the spine which in turn requires cutting and displacing major muscles and ligaments surrounding the spine. Such procedures are necessarily performed under a general anesthesia and may require hospital stays. Recovery times vary from weeks to months and extensive rehabilitation is usually necessary.

For these reasons, it would be desirable to provide methods and tools for performing less invasive interventions to treat spinal stenosis. It would be particularly desirable if such protocols could utilize relatively small access cannuli and could be performed under external and/or endoscopic visualization. At least some of these objectives will be met by the inventions described hereinbelow.

2. Description of the Background Art

US2009/0036936 and US2008/0221383 describe minimally invasive procedures for treating spinal stenosis by percutaneously accessing the epidural space. US 2005/197661 describes a rotating bone burr and use of the bone burr in performing a laminectomy. The tool is introduced through an incision in the back. Other patents and published applications of interest include U.S. Pat. Nos. 6,740,090; 6,258,093; 6,174,313; 5,755,718; US 2008/071282; US 2006/217728; and US 2006/004369.

BRIEF SUMMARY OF THE INVENTION

The present invention provides methods, apparatus, and systems for the minimally invasive treatment of spinal stenosis. In particular, methods are provided for laterally decompressing one or more spinal nerve(s) adjacent to a target facet joint in the lumbar spine of a patient. A tool guide is percutaneously positioned through an access penetration to an anterior surface of a superior articular process of the facet joint. A bone removal tool is advanced over the tool guide through the access penetration, and bone is removed using the bone removal tool to relieve pressure on one or more spinal nerve(s).

The following words and phrases will have the following definitions when used in the claims and specification of this application.

Spinal nerve(s) will include the nerves of the cauda equina, the transversing nerve, and the exiting nerve. The traversing and exiting nerves are also referred to as nerve roots exiting from the cauda equina which is present in the epidural region of the lumbar spine.

Percutaneous access refers to a minimally invasive procedure for laterally accessing the target facet joint by placing an access cannula or sheath which provides a central access passage. Typically, the access cannula or sheath is placed using needles and dilators to form a percutaneous access track in which the access cannula or sheath is placed. Alternatively, a small surgical incision can be made to provide the percutaneous access.

The phrase "tool guide" refers to an elongate structure which is placed through a percutaneous access tract, typically through an access sheath or cannula within the tract, to provide a guidance path for the subsequent introduction of a bone removal tool. The tool guide will extend through the access cannula or sheath to and optionally past the anterior surface of the superior articular process of the target facet joint. The tool guide will typically be advanced into the epidural space. In a first exemplary embodiment, one and sometimes two or more guidewire(s) will be placed through the access sheath, for example, with a first guidewire extending in a cephalad direction (toward the patient's head) and a second guidewire extending in a caudal direction (toward the patient's feet). In a second exemplary embodiment, a guide track having a ribbon-like base and at least one axial rail on a surface of the base may be used where the bone removal tool will have a channel or other structure for riding on or over the rail for guidance.

The phrase "bone removal tool" will refer to any tool which may be percutaneously advanced through the guide cannula or sheath and which may be manipulated within the sheath to remove bone from the anterior surface of the inferior articular process of the facet joint. An exemplary bone removal tool incorporates a high speed burr for removing bone by abrasion. Other bone removal tools can incorporate blades for cutting bone, radiofrequency elements for ablating bone, or the like.

The phrase "facet joint" refers to the zygapophysial joint, which is a synovial joint between the superior articular process of an inferior vertebra, and the inferior articular process of a superior vertebra in a patient's spine. The facet joints stabilize the spine by supporting vertically adjacent vertebrae while allowing them to rotate. The present invention is directed particularly at removing bone from the anterior or forward surface of the superior articular process of the joint although in some cases a portion of the inferior articular process may also be removed if it impinges on a spinal nerve. The anterior surface is opposed to the vertebral disk disposed between the superior and inferior vertebrae and it adjacent to the ligamentum flavum which surrounds the epidural sac and cauda equina.

The phrase "ligamentum flavum" refers to the ligament which connects the lamina of a vertically adjacent vertebra in the patient's spine. The ligamentum flavum directly overlies the spinal canal and epidural sac and is also attached to the facet capsule.

The methods of the present invention are directed at relieving pressure from at least one spinal nerve, including nerves of the cauda equina, as well as exiting nerves and transversing nerves which may extend from the cauda equina.

The methods of the present invention typically rely on minimally invasively placing an access sheath to provide the access penetration for the tool guide. A Seldinger or other conventional lateral access technique can be used, such as advancing a hollow needle percutaneously to position a distal end of a needle at the target facet joint. A sheath placement guidewire is positioned through the needle, and the needle removed to leave the sheath placement guidewire in place. One or more dilators are then advanced over the sheath placement guidewire to enlarge the percutaneous tract to a desired target size, typically in the range from 6 mm to 10 mm. Once the access track has been enlarged sufficiently, the access sheath may be placed over the dilator and the sheath placement guidewire removed to leave the sheath in place, providing a dilated percutaneous tract.

The tool guide which is percutaneously positioned through the access penetration may include one or more guidewires. The guidewire(s) will typically be advanced through the access sheath and into the epidural region. Often, at least two guidewires will be employed, with one guidewire placed in a cephalad direction and another guidewire placed in a caudal direction. Optionally, the guidewire(s) may be anchored within the epidural region, typically by expanding a balloon or other expandable anchor. The tool guides will usually be observable under fluoroscopic or other imaging, typically being all or partially radiopaque or radiolucent with radiopaque marker(s).

Once the guidewire(s) are in place, the bone removal tool may be advanced over the guidewire(s). In order to achieve removal of a sufficient volume and/or area of bone, the guidewire(s) may be repositioned one or more times so that the bone removal tool can follow a different path adjacent the anterior surface of the articular process. The guidewires will often be steerable, e.g. having a pre-formed or shapeable tip to allow placement of the removed tool. The guidewires could also have deflectable tips to allow active positioning of the bone removal tool.

Alternatively, the tool guide of the present invention may comprise a guide track having a base which is wide relative to its thickness, e.g. in the form of a ribbon. A posterior surface of the guide track will include at least one rail, optionally two, and preferably three rails, so that the guide track may be positioned with the base adjacent a disk and the bone removal tool advanced over the rail(s) which are adjacent the anterior surface of the articular process. In this way, the base protects the disk as the removal tool is advanced over the rail to remove bone. The use of two, three, or more rails allows the bone removal tool to be sequentially advanced over the rails to remove successive segments of the bone to achieve the desired area and/or volume of bone removal. Optionally, the guide track could be repositioned one or more times, but repositioning will usually be unnecessary when multiple rails are utilized.

The bone removal tool can be any tool suitable for percutaneous introduction, as defined above, and having the capability of removing a controlled volume and area of bone from the anterior surface of the superior articular process of the facet joint. Preferably, the bone removal tool will be visually observable under external or endoscopic imaging to permit the treating physician to see how much bone has been removed. In the exemplary embodiments, the bone removal tool includes a rotating burr which can be engaged against the anterior surface of the superior articular process to grind the bone into small pieces which can be removed by flushing with saline or other suitable irrigant. The surface of the rotating burr may be embedded with diamond or other abrasive material. Alternatively, the rotating burr surface may have flutes or other cutting features incorporated into its surface. The tool will usually be adapted to rotate the burr at a speed in the range from 25,000 rpm to 125,000 rpm. Optionally, the tool may have both distally and proximally disposed abrasive or cutting surfaces, e.g. a rounded head, so that the tool be reciprocated (alternately advanced and retracted) over the articular surface to remove the impinging material. Further optionally, the burr or other rotational abrasive or cutting element may be rotated in a single rotational direction or the direction of rotation may be periodically reversed. Usually, a cooling and/or flushing medium will be introduced to the rotating burr in order to remove heat and optionally permit aspiration of the removed bone material. Still further optionally, the burr may be replaced during the procedure, either to permit replacement of a worn burr or more usually to allow use of a larger burr in order to remove a greater area and/or volume of the bone material. In the exemplary embodiments, a first burr having a diameter in the range from 1 mm to 3 mm is used followed by one or more successive burrs having larger diameters up to a range from 5 mm to 10 mm.

Often, once a desired amount of the anterior surface of the articular process has been removed, sufficient decompression of the spinal nerve(s) will be achieved. In other instances, however, compression against the spinal nerve(s) may still be present, usually being caused by the ligamentum flavum pressing against a spinal nerve(s). The treating physician may assess this condition and may optionally cut the ligamentum flavum to further relieve pressure on the spinal nerve(s). The ligamentum flavum will typically be cut in a region which relieves pressure from the transversing or exiting spinal nerve, and cutting will usually be performed while imaging the target facet joint and the surrounding tissue while positioning and advancing a cutting tool. Imaging is typically performed externally, for example using fluoroscopy, computer tomography, or magnetic resonance imaging, or performed endoscopically used an optical scope positioned through the access penetration.

The present invention further comprises systems for laterally decompressing one or more spinal nerve(s) adjacent to a target facet joint in the lumbar space of a patient. Such systems comprise an access sheath, a tool guide, and a bone removal tool. The access sheath has a central passage and is positionable through a percutaneous access penetration which extends from the patient's side to an anterior surface of the superior articular process of the facet joint. The tool guide is positionable through a central passage of the access sheath, and the bone removal tool is advanceable through the access sheath and over the tool guide. The bone removal tool will have an end effector which can remove bone when engaged against said bone.

The access sheath of the system of the present invention will typically be a tubular cannula having a distal end and a proximal end. Preferably, the distal end is formed with a recess or other asymmetric geometry which provides a distally extending tip which is configured to engage a disk adjacent to the facet joint. The distally extending tip can protect the disk while a recess exposes articular surface of the facet joint for engagement by the end effector of the bone removal tool. Usually, the recessed distal end of the access sheath comprises a simple chamfer at an angle from 30° to 60° relative to the axial direction. Other asymmetric designs having one side of the cannula extending further than the opposite side could also find use.

The tool guides of the systems of the present invention may comprise guidewire(s), guide tracks, or other elongate structures which provide a guide path over which the bone removal tool may be advanced. When using guidewires, the system may include two or more guidewires so that one guidewire may be positioned in a cephalad direction and the other guidewire simultaneously positioned in a caudal direction. The guidewires may optionally include balloons or other anchors at their distal ends to maintain stability while the bone removal tool is being advanced thereover.

The tool guide may alternatively comprise a guide track having a base which is wide relative to its thickness and including at least one rail on a posterior surface thereof. The wide or ribbon-like structure provides lateral rigidity while permitting flexibility in the orthogonal direction. In this way, the guide track may be advanced through the access sheath with the posterior surface advancing through the space available between patient disk and the articular process being treated. The guide track may curve or otherwise conform to the region between the disk and articular process to allow advancement of the bone cutting tool over the rail while protecting the disk. The use of two, three, or more rails allows the cutting tool to be advanced in successive passes in order to remove additional bone.

The bone removal tool is typically a shaft having a rotating burr at its distal end. The tool will further include a motor and a driveshaft coupling the motor to the rotating burr. The motor will be adapted to rotate the burr at a speed sufficient to abrade and remove bone, typically in the range from 25,000 to 125,000 rpm. When deployed over a guidewire, the bone removal tool will include a guidewire lumen. Preferably, the guidewire lumen will be coaxially positioned within the bone removal tool, extending through a center of the rotating burr and through the rotating driveshaft. Alternatively, the guidewire may be laterally deployed along one side of the bone removal tool. In the latter case, the tool will preferably include a spatula or other distally extending structure to protect the guidewire from the rotating burr as the tool is advanced over the guidewire.

The systems of the present invention will preferably also include a tool for cutting the ligamentum flavum after bone has been removed by the bone removal tool. The tool will preferably include a shaft or handle having a cutting blade at its distal end. The cutting tool will preferably include a retractable protector surrounding the blade. The protector will typically be spring-loaded so that it retracts as the blade is advanced through the ligamentum flavum but automatically redeploys to surround and protect the blade when the blade is removed from the ligamentum flavum.

BRIEF DESCRIPTION OF THE DRAWINGS

FIG. 1 illustrates a system for removing bone from a facet joint, where the system includes a tool guide, a bone removal tool, and an access sheath.

FIGS. 2A and 2B illustrate alternative distal end configurations for the access sheath of the system of FIG. 1.

FIGS. 3 and 3A illustrate alternative configurations for the bone removal tool of the system of FIG. 1.

FIGS. 4-7 illustrate alternative configurations for the tool guide of the system of FIG. 1.

FIG. 8 illustrates a tool for cutting a ligamentum flavum which may be optionally included in the systems of the present invention.

FIGS. 9A and 9B illustrate the automatic retraction of a blade protector of the cutting tool of FIG. 8.

FIGS. 12A and 12B-19A and 19B illustrate a first treatment protocol in accordance with the present invention.

FIGS. 20A and 20B-22A and 22B illustrate a second treatment protocol in accordance with the principles of the present invention.

DETAILED DESCRIPTION OF THE INVENTION

Figure 10A:
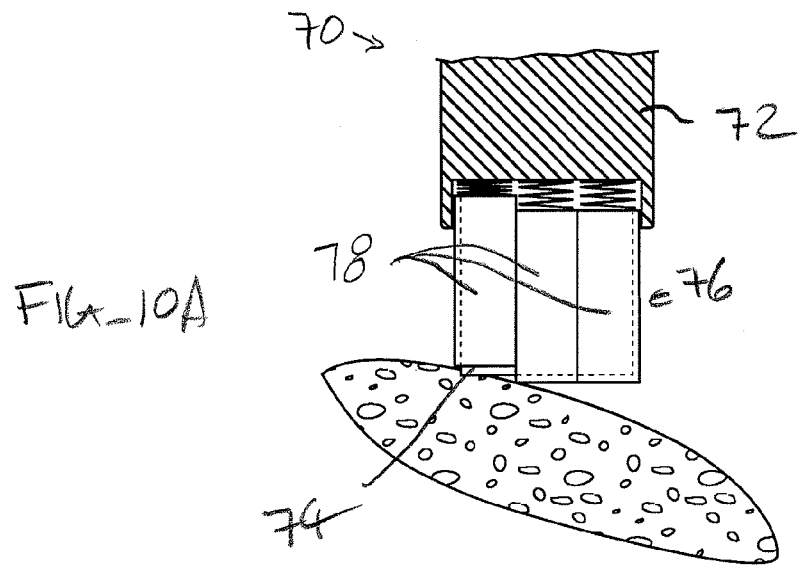
FIGS. 10A-10C are cross-sectional views illustrating how the blade protector of FIGS. 9A and 9B operates.

A system for laterally decompressing spinal nerve(s) in accordance with the principles of the present invention is illustrated in FIG. 1. System 10 includes a tool guide 12, illustrated as a guidewire, a bone removal tool 14, and an access sheath 16. The bone removal tool 14 includes a body 18 which can be manually grasped to allow manipulation of the tool, a drive motor 20, and a connecting cable 22. The connecting cable 22 includes an outer cover and an inner driveshaft which is connected to a rotatable cutting or boring element, such as a rotating burr 24, which is driven and axially translated by the motor 20. Usually, a source 26 of saline or other irrigant liquid is provided and connected to the tool body 14 by a feed tube 28. In this way, the saline may be delivered through an axial passage in the body 18 so that it may be delivered about the periphery of the burr 24, as indicated by arrows 30. In use, the motor 20 will rotate the burr 24, typically at a rotational speed in the ranges set forth above. Additionally, the burr may be axially advanced and retracted using a control mechanism 32 which may be advanced and retracted as indicated by arrow 34 to advance and retract the drive shaft and the burr head, as indicated by arrow 36.

The access sheath 16 will typically comprise a tubular cannula, typically having a length in the range from 10 cm to 50 cm and a diameter in the range from 4 mm to 12 mm. A distal end 40 of the cannula 38 will be formed asymmetrically to provide a recessed working space while protecting the patient's existing nerve root from contact with the burr, as will be described in more detail below. The distal end may conveniently be formed as a simple chamfer, as shown in FIG. 1, or may alternatively have other recessed configurations, such as a curved recess 42, as shown in FIG. 2A or a stepped recess 44, as shown in FIG. 2B.

As shown in FIG. 1, the bone removal tool 14 is adapted to be introduced over a guidewire 12, where the guidewire is received through a guidewire lumen 46 formed centrally through the rotating burr 24 and coaxially through the driveshaft and cable 22. Use of the central, coaxial guidewire is advantageous since it increases the stability of the bone removal tool 14 as it is advanced and decreases the likelihood of whipping and other instability.

In other cases, however, it may be desirable to provide a bone removal tool 14' having a rotating burr 24' which does not include a guidewire port, as illustrated in FIG. 3. The bone removal tool 14', instead, includes a separate guidewire lumen 48 along one side of the body 18'. Such an "eccentric" guidewire lumen can be advantageous since it can guide the burr further into the bone and remove more bone without increasing the size of the bone removal tool. As passage of the guidewire along the side of the tool 14' will expose the guidewire to the rotating burr 24', it is necessary to provide a protecting member. In some instances, the guidewire tube 48 may be sufficient to provide protection by extending the distal end 50 of the tube beyond the rotating burr 24'. Preferably, however, a spatula 52 or other protective element will also be provided between the rotating burr 24 and the guidewire 12 and guidewire tube 48. Provision of the protective spatula 12 will also protect the patient's disk and other structures, although the principal protection will be provided by the access sheath 16, as described in more detail below. In still other embodiments, the rotatable cutting or boring element can be a fluted cutter 31 (FIG. 3A) of the type described in U.S. Pat. No. 4,445,509, the full disclosure of which is incorporated herein by reference.

Referring now to FIGS. 4-7, an alternative tool guide will be described. The tool guide of FIG. 1 is a guidewire which passes coaxially through the bone removal tool 14 (FIG. 1) or laterally along one side of the bone removal tool 14' (FIG. 3). In addition to these constructions, the guide tool could be a guide track 54 having at least one rail 56 formed on a posterior surface 58 thereof. The body 18" includes a channel 60 which has a shape which is complementary to the exterior of the rail 56. As shown, both the rail 56 and channel 60 have a T-shaped geometry, but other configurations could be used as well. The body 18" of the bone removal tool 14" can thus be advanced over the rail 56 of the guide track 54 replacing the channel 60 over the rail.

The guide track 54 may have a solid body, as illustrated in FIG. 5, but will more usually include a lumen 62 for receiving a guidewire. In some instances, once an adequate percutaneous penetration has been formed, the guide track 54 may be introduced directly over a guidewire (not within an access sheath) where the base 58 of the track 54 provides sufficient protection for the patient's disk. Usually, however, the guide track 54 will be introduced through the access sheath and the guide track will provide supplemental protection of the disk. A particular advantage of the use of a guide track 54 having a relatively wide base 55 is that multiple rails 56 may be positioned on the posterior surface 58, as illustrated in FIG. 7.

Referring now to FIG. 8, system 10 of the present invention may optionally further include a tool 70 adapted for cutting the ligamentum flavum. The tool will include a body or handle 72 which may be manually gripped and used by the treating physician. The tool 70 will further include a cutting blade 74 protected on either side by a retractable protector assembly 76. As shown in FIGS. 9A and 9B, the tool 70 is initially engaged against the ligamentum flavum LF with the distal edge of the retractable protector assembly first contacting the surface of the ligamentum flavum. The retractable protector assembly may comprise one, two, three or more retractable segments 78, for example three, where each segment retracts sufficiently (in response to the force applied when entering the ligamentum flavum) to allow the fixed blade 74 to cut into the ligamentum flavum LF while limiting the depth of cutting and protecting other tissue structures.

Figure 10B:
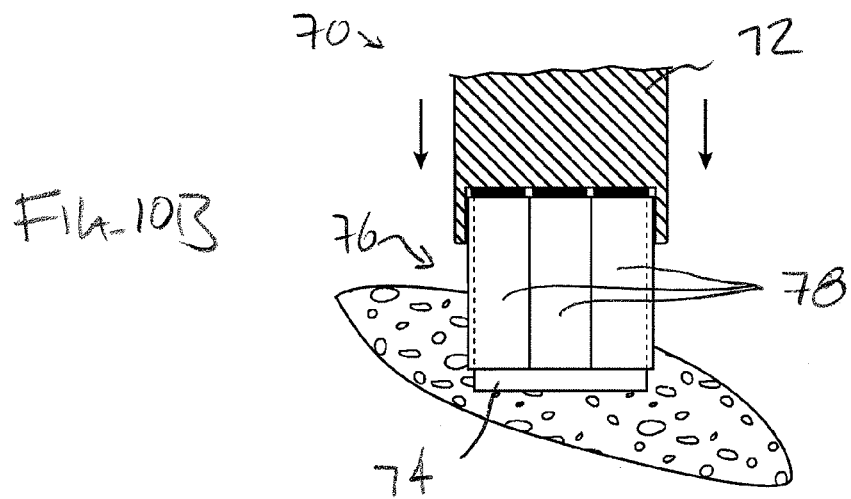
Figure 10C:
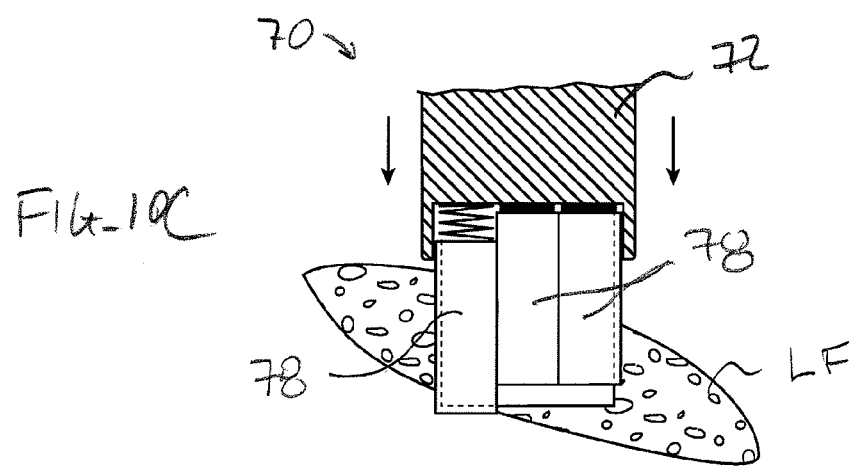

Functioning of the retractable protector assembly 76 of the ligamentum flavum cutting tool 70 is illustrated in FIGS. 10A-10C. Each of the segments 78 of the protector assembly 76 is independently spring mounted, so that segment individually retracts as it first engages the surface of the ligamentum flavum LF, as shown in FIG. 10A. Once the blade is entirely within the ligamentum flavum, as illustrated in FIG. 10B, the individual segments 78 will be fully retracted, which in turn fully exposes the blade 74. As the tool 70 is further advanced, a portion of the blade exits from the ligamentum flavum LF, as shown in FIG. 10C, and the segment 78 covering that portion of the blade immediately advances to cover and protect the blade (as the force applied by the ligamentum flavum is released). The remaining segments, however, remain retracted to allow continued cutting of the remaining ligamentum flavum LF.

Figure 11A:
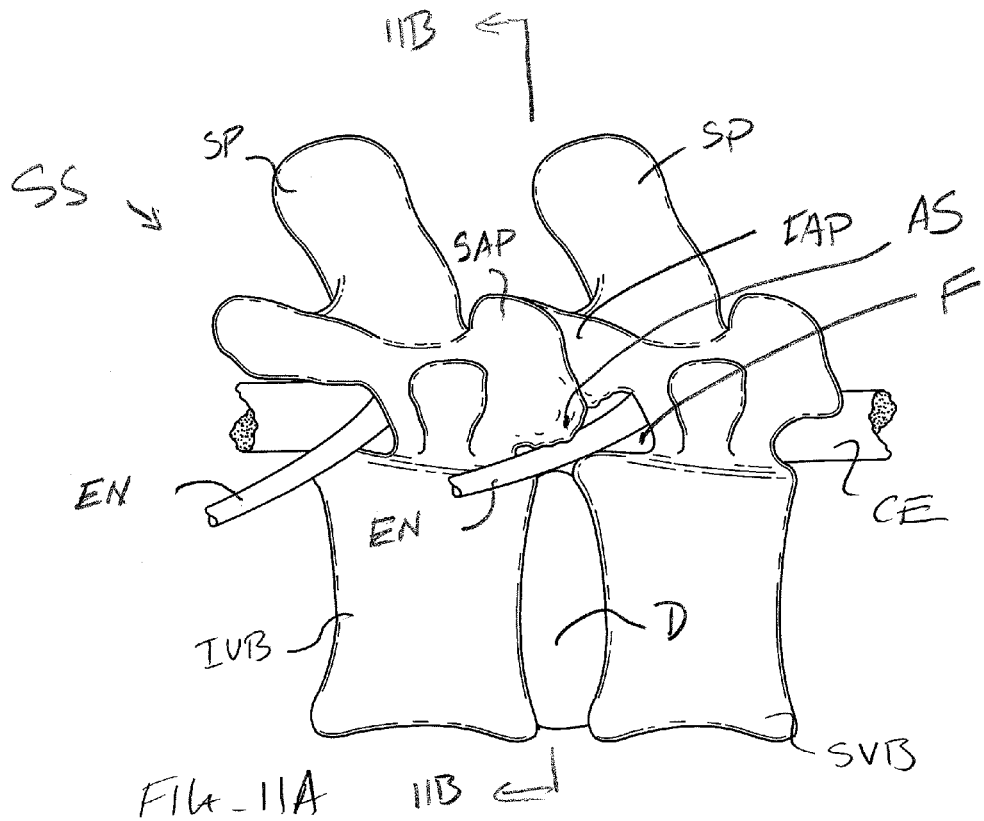
FIGS. 11A and 11B illustrate the anatomy of a facet joint including the articular processes, vertebral bodies, and disk present in a spinal segment.
Figure 11B:
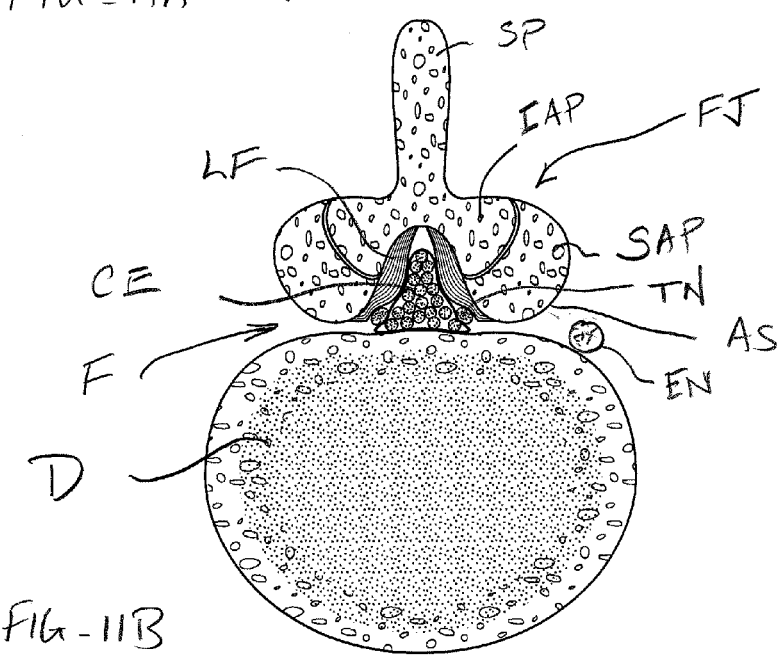

FIGS. 11A and 11B illustrate the anatomy of a spinal segment SS including a superior vertebral body SVB and an inferior vertebral body IVB. A disk D is captured between the vertebral bodies and, as best seen in FIG. 11B, the facet joint FJ is generally disposed on the posterior (which is the top in FIG. 11B) side of the disk. The facet joint is formed between a surface of the superior articular process SAP and a surface of the inferior articular process IAP. The spinal nerves of the cauda equina CE extend through the foramen F and are engaged by the ligamentum flavum LF, again as best seen in FIG. 11B. Of particular interest to the present invention, a transversing nerve TN exiting from the cauda equina can be pinched between the ligamentum flavum and the cauda equina. An exiting nerve EN can also be compressed by the anterior surface AS or superior overgrowth of the superior articular process SAP.

Figure 12A:
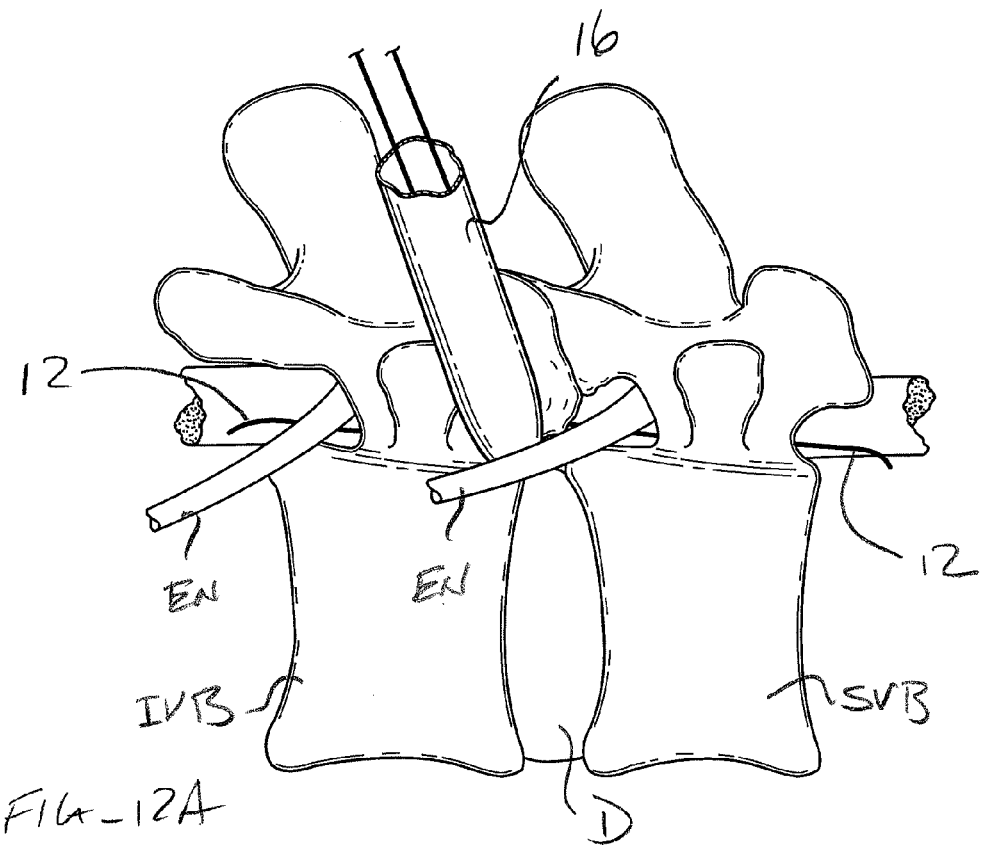
Figure 12B:
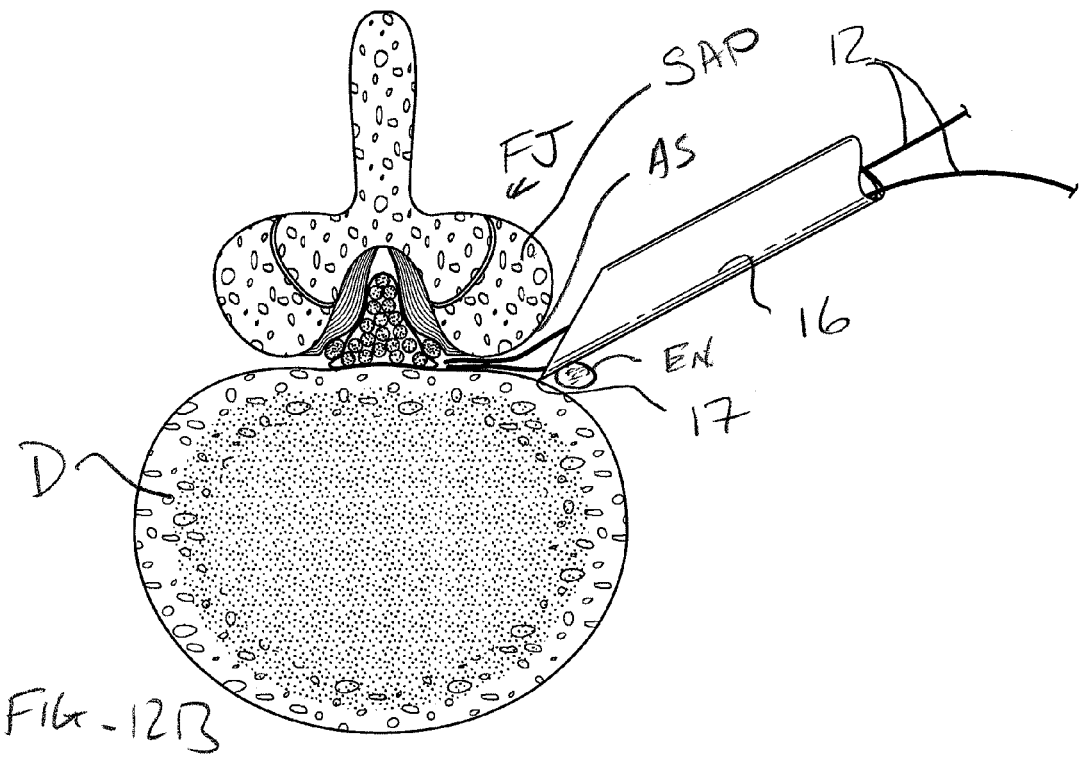

A first protocol for relieving compression of these spinal nerve(s), including the nerves of the cauda equina CE, the transversing nerves TN, and the exiting nerves EN is illustrated in FIGS. 12A and 12B-19A and 19B. As shown in FIGS. 12A and 12B, the access sheath 16 is initially placed through a percutaneous access tract formed in a conventional manner, typically using a Seldinger needle exchange and sequential dilation. The access sheath 16 is positioned so that its distal tip 17 engages the disk D to provide a protected entry route to the region of the facet joint FJ. At least one guidewire is introduced through the access sheath 16. As shown in FIG. 12A, first and second guidewires 12 are introduced in the cephalad direction and the caudal direction. Both guidewires pass by the anterior surface AS of the superior articular process SAP.

The access sheath 16 is preferably placed so that it lies over the exiting nerve EN to protect the nerve from damage from the bone cutting tool, as described below.

Figure 13A:
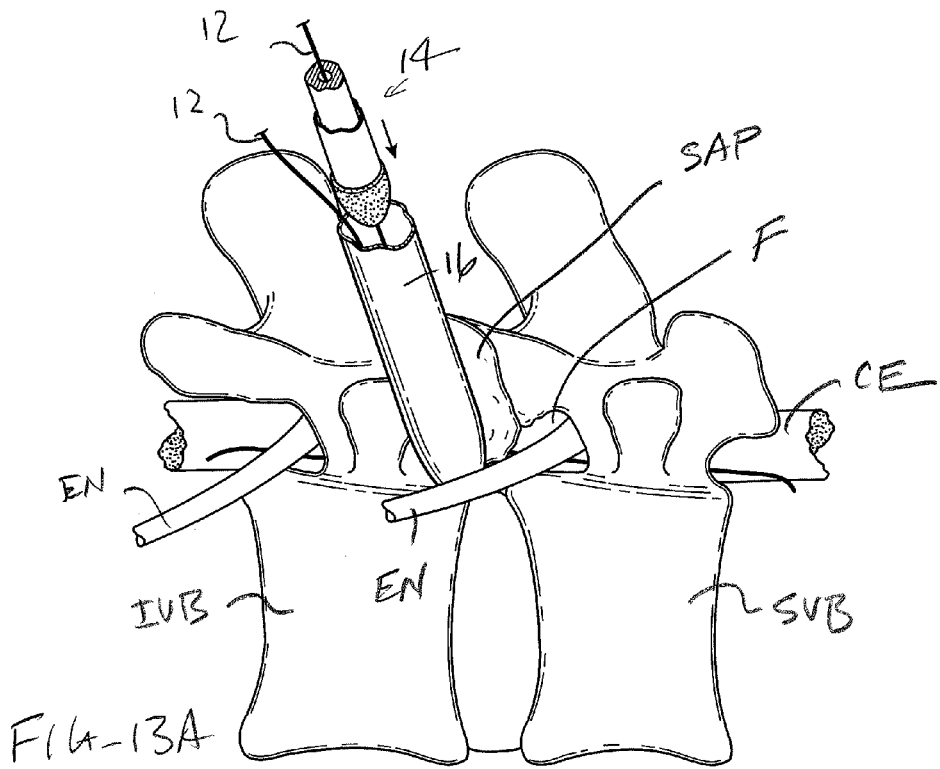
Figure 13B:
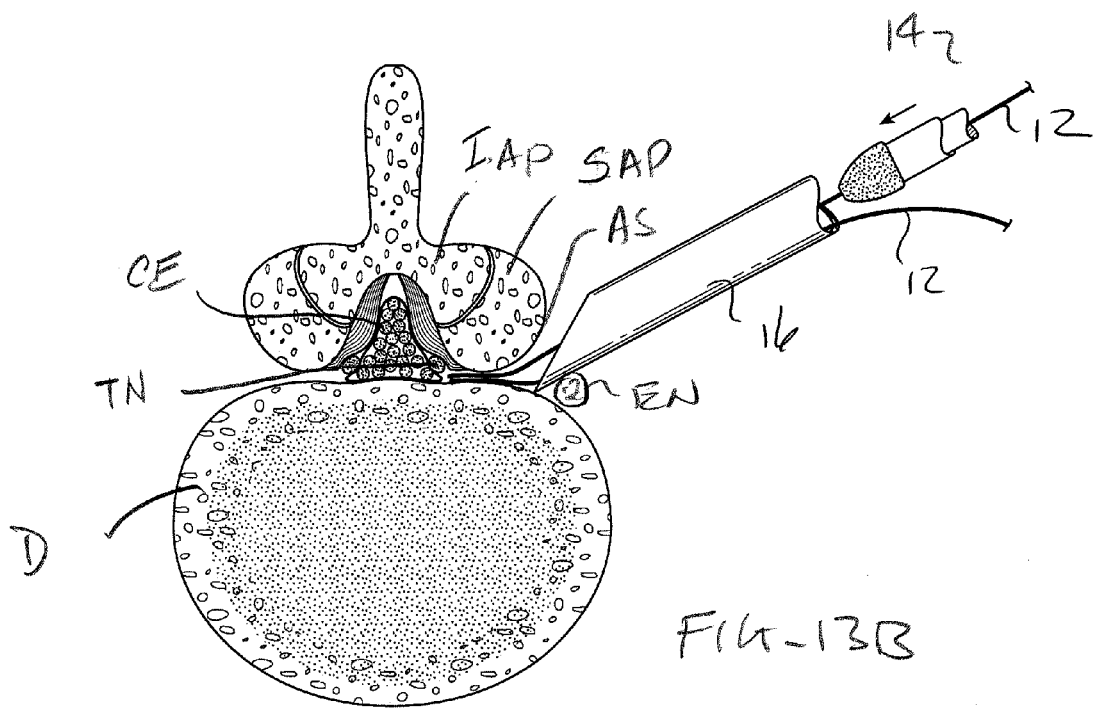

Once the access sheath 16 is in place, the bone removal tool 14 can be advanced over a first of the two guidewires, as shown in FIGS. 13A/B. The second guidewire 12 remains in place through the sheath for use in a subsequent portion of the protocol.

Figure 14A:
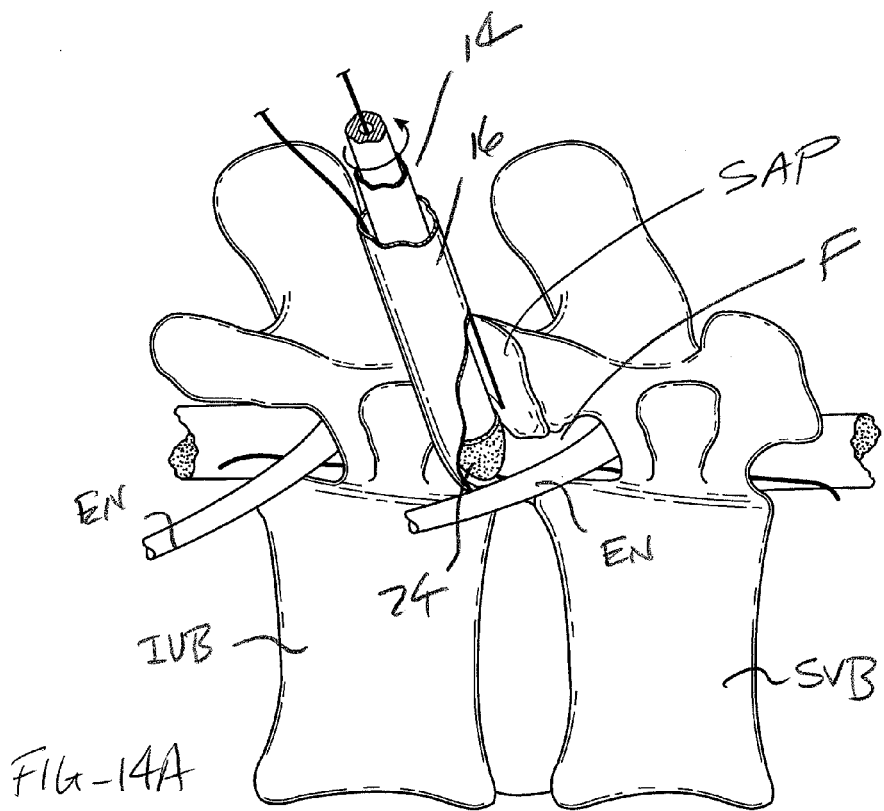
Figure 14B:
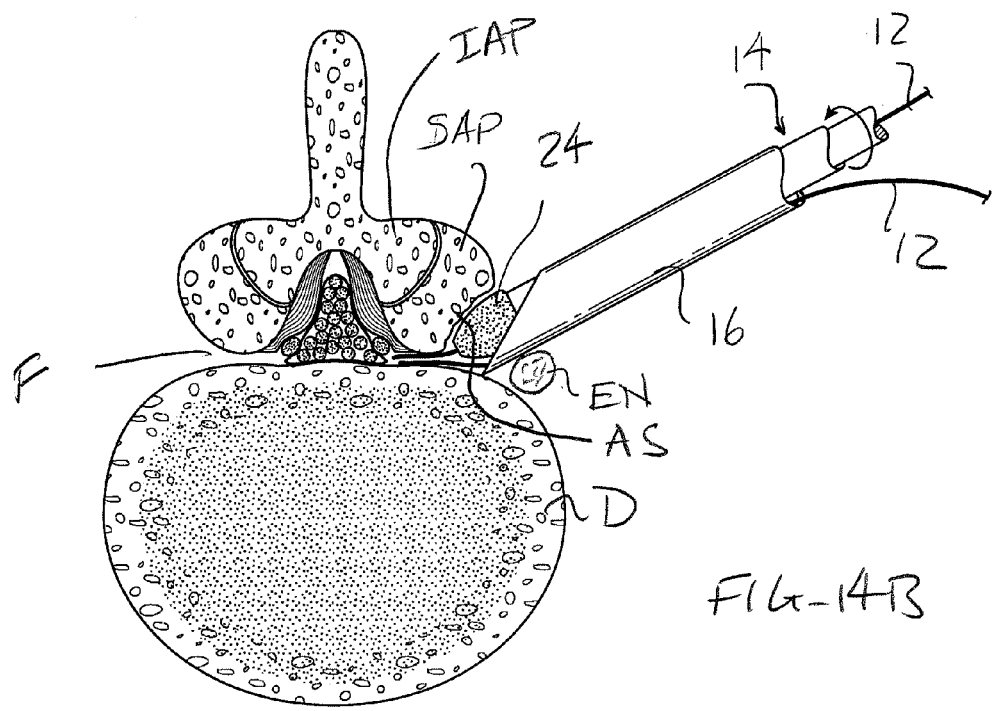

As shown in FIGS. 14A/B, the bone removal tool 14 is advanced so that the rotating burr 24 is engaged against the anterior surface AS of the superior articular process SAP so that rotation of the burr removes the bone material, as best seen in FIG. 14B. The burr is exposed to the bone through the open or recessed distal end of the access sheath 16 while the extending tip of the sheath partially protects the disk D and exiting nerve EN.

Figure 15A:
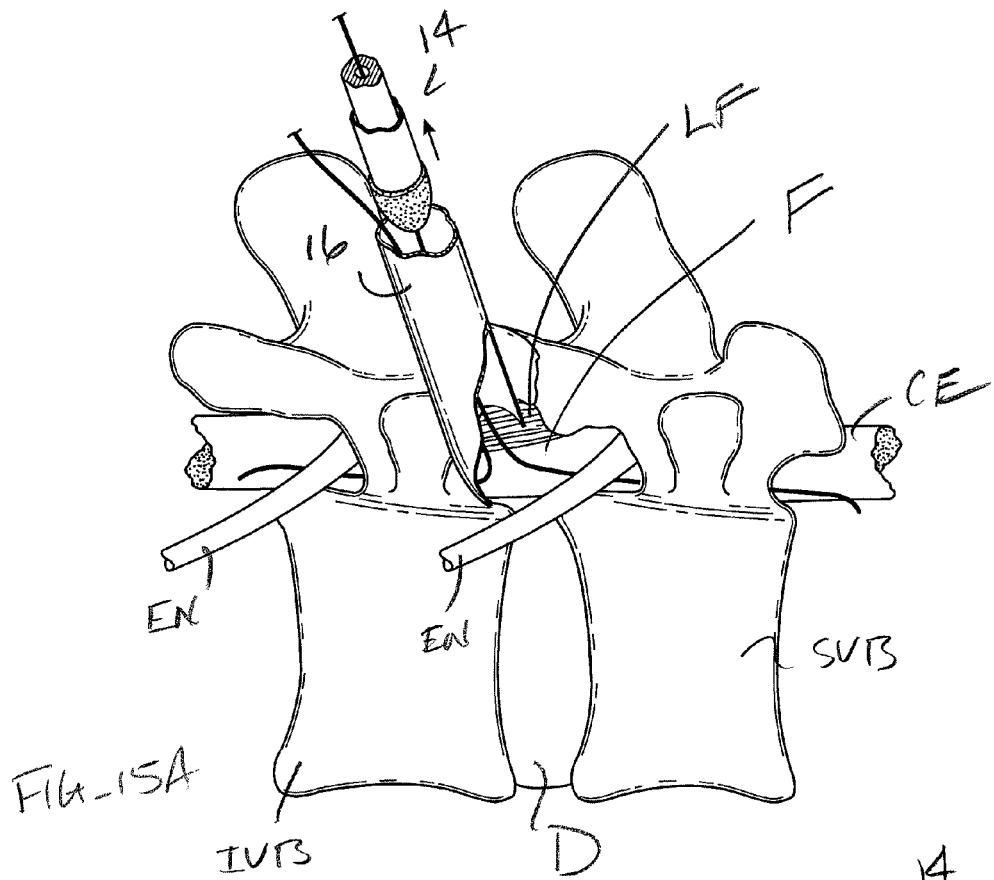
Figure 15B:
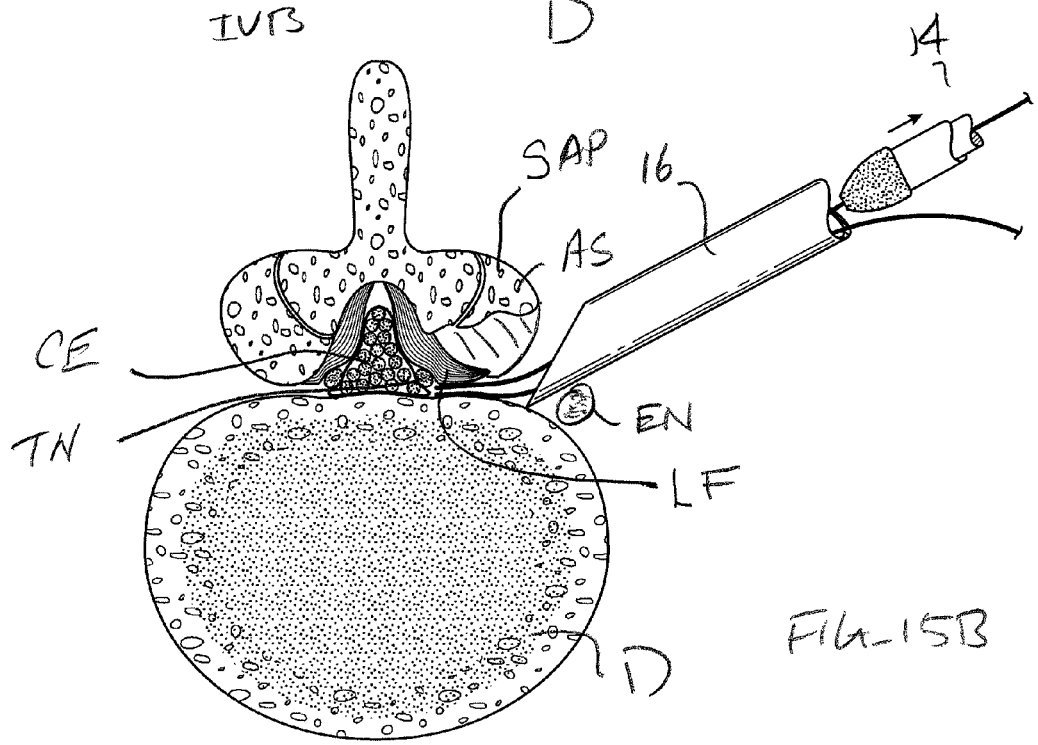

Referring now to FIGS. 15A/B, the bone removal tool 14 is removed from the access sheath 16 after a sufficient portion of bone has been removed to relieve pressure on the spinal nerve(s). As shown in FIG. 15B, a significant volume of the anterior surface AS of the superior articular process SAP has been removed, freeing or mobilizing the ligamentum flavum LF over the transversing nerve TN and cauda equina CE. In many cases, the removal of the bone will be sufficient to relieve compression of the spinal nerve(s) and the procedure can be terminated at this point.

After cutting tool 14 has been introduced over the first guidewire 12 and used to remove bone, it will usually be then introduced over the second guidewire 12 (or the first guidewire may be repositioned) to reduce bone in a second segment or region adjacent to where the bone was first removed. In particular, by positioning the two guidewires in a cephalad and caudal direction, respectively, the first guidewire may be used to remove bone on a cephalad side of the articular surface while the second guidewire may be used to remove bone on a caudal side of the articular surface. It will be appreciated that further guidewires may be utilized to remove other regions or that the guidewire(s) may be repositioned to remove bone in other regions.

After a desired volume of bone has been removed, the treating physician will visually assess the spinal nerve(s) and determine that compression may still be caused by the ligamentum flavum LF. In those cases, additional steps will be taken to cut the ligamentum flavum LF to additionally relieve nerve compression, as shown in FIG. 16A/B-19 A/B.

Figure 17A:
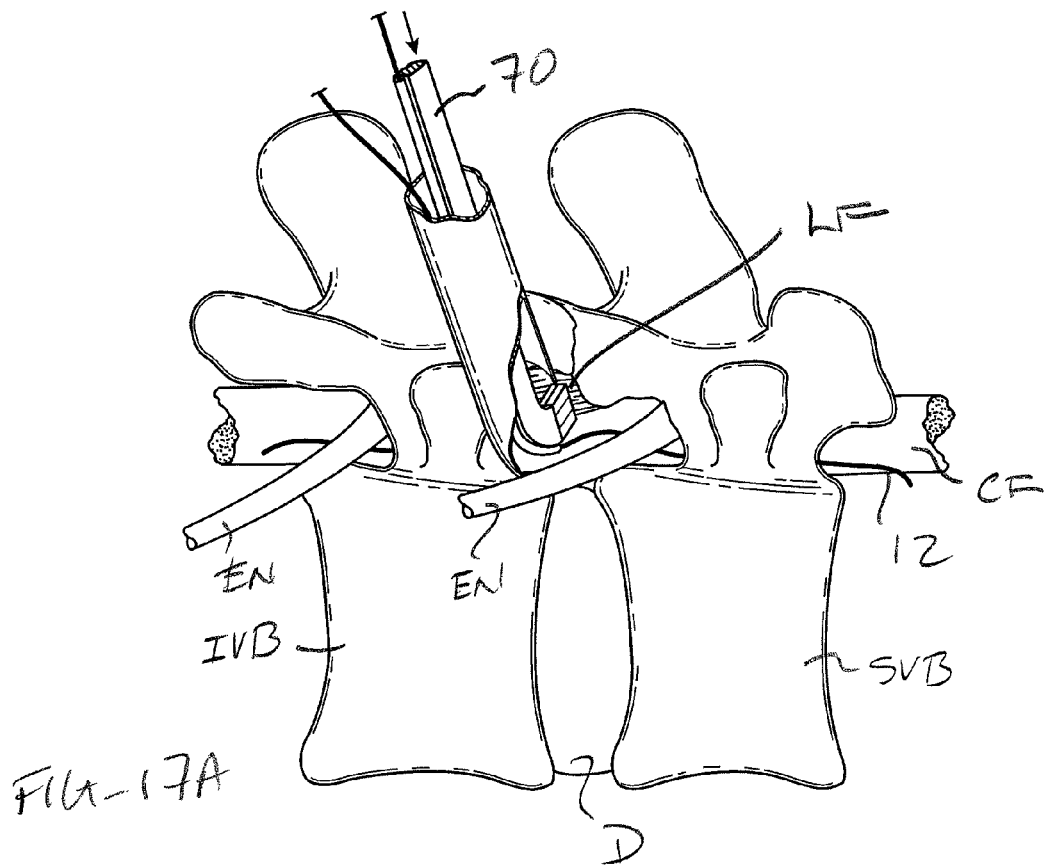
Figure 17B:
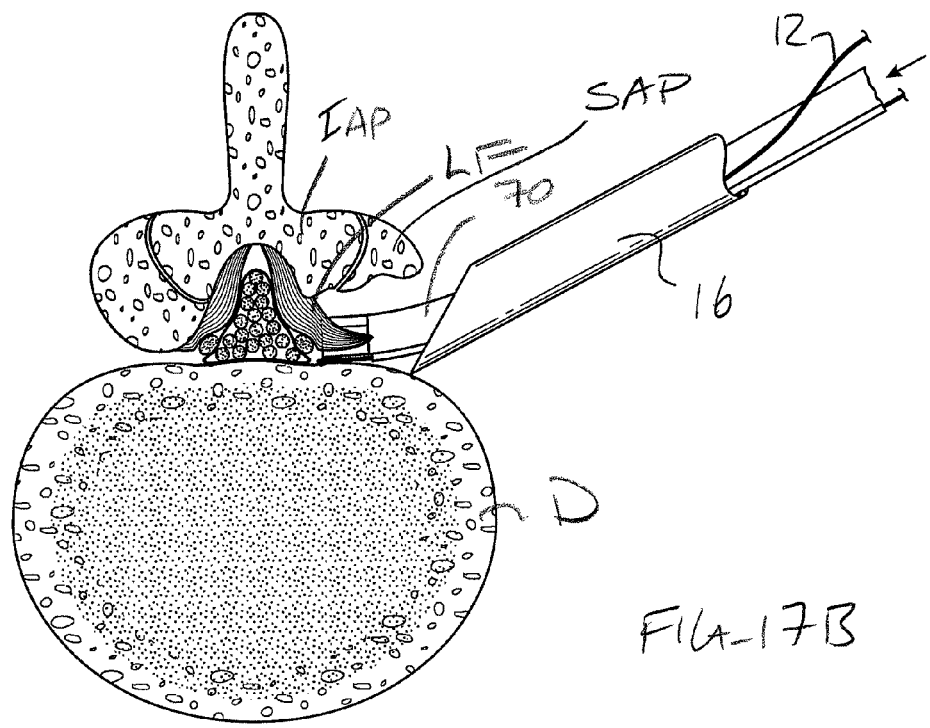
Figure 18A:
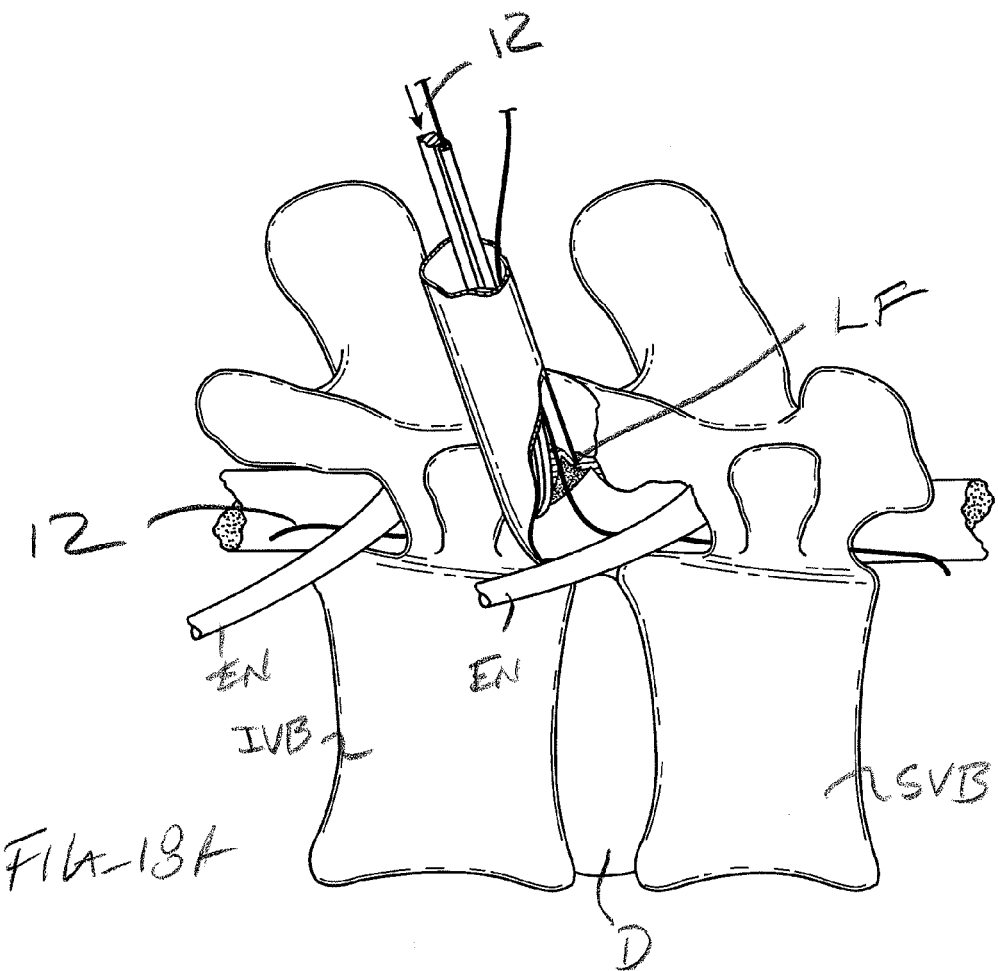
Figure 18B:
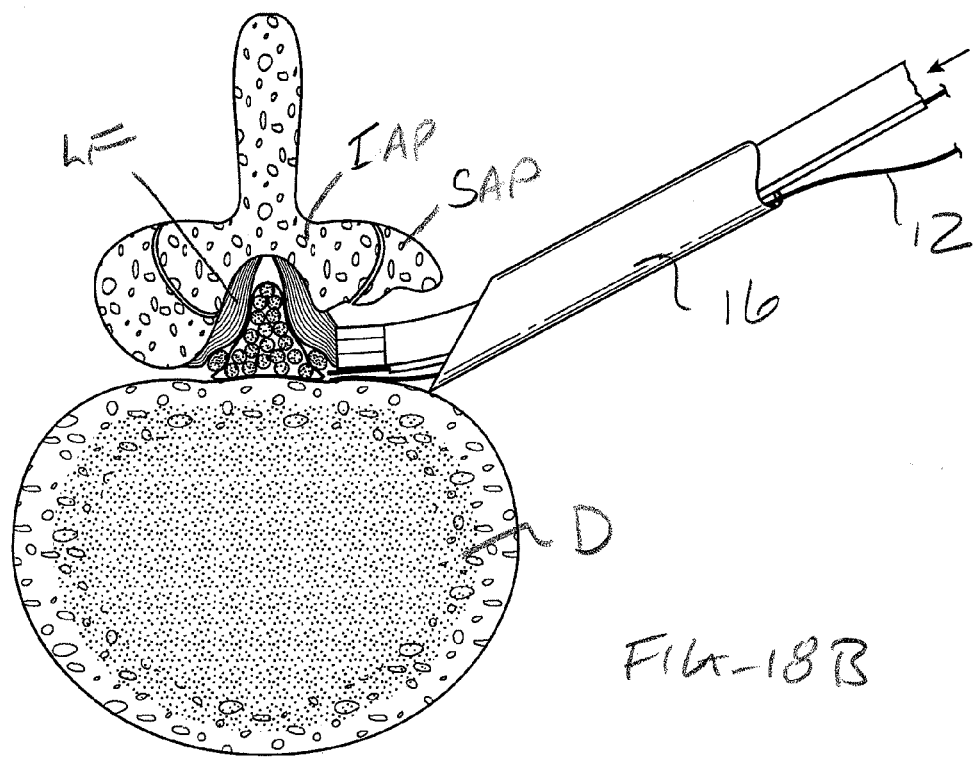
Figure 19A:
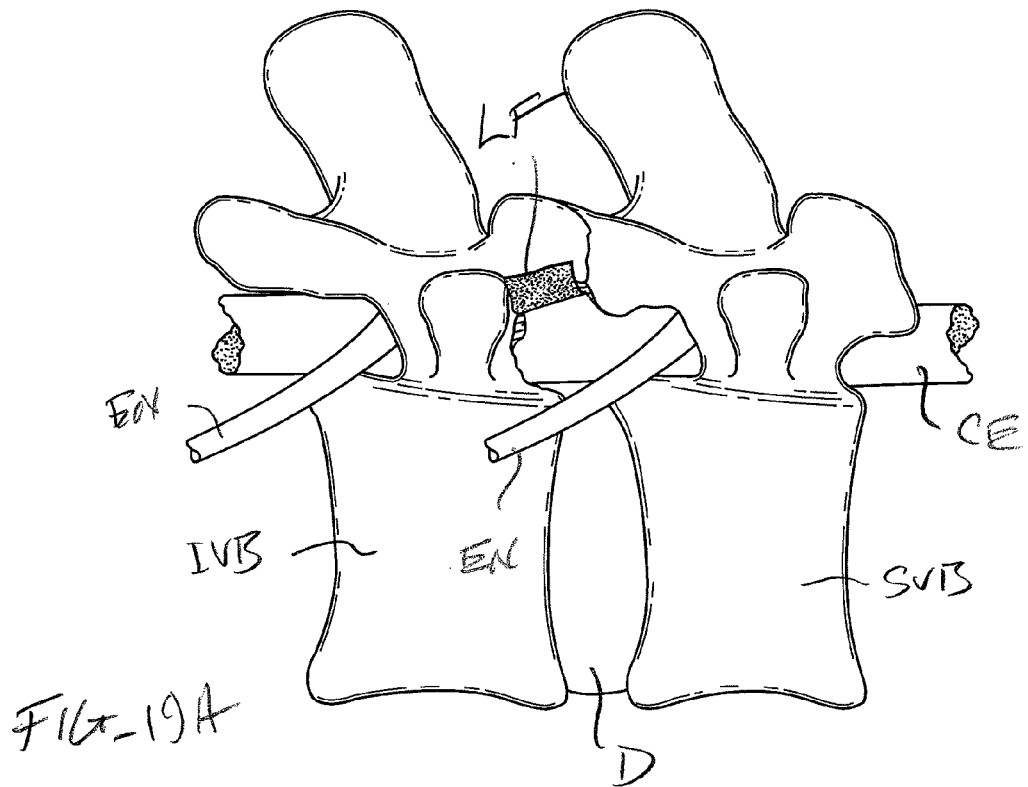
Figure 19B:
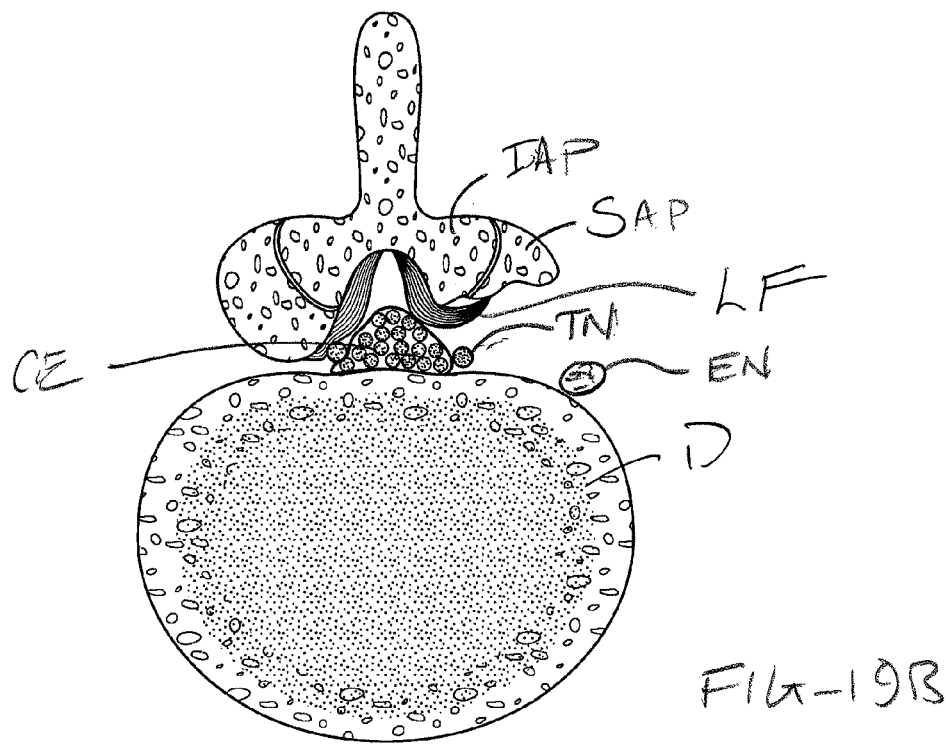

As shown in FIGS. 16A and 16B, the cutting tool 70 may be introduced through the access sheath 16 over a first of the guidewires 12. The tool is advanced so that its distal end engages the ligamentum flavum LF (as illustrated in FIG. 17A/B). Optionally, the distal end of the cutting tool may be steerable or deflectable in order to facilitate proper positioning of the blade. The cutting tool is advanced so that the blade will cut into the ligamentum flavum LF, as shown in FIGS. 18A/B and optionally the tool will be introduced over the second guidewire 12 in order to provide two cuts through the ligamentum flavum LF, providing an open flap FL, as best seen in FIG. 19B. The cutting tool, guidewires, and access sheath may then be removed and the tissue access tract closed to end the procedure.

Figure 21A:
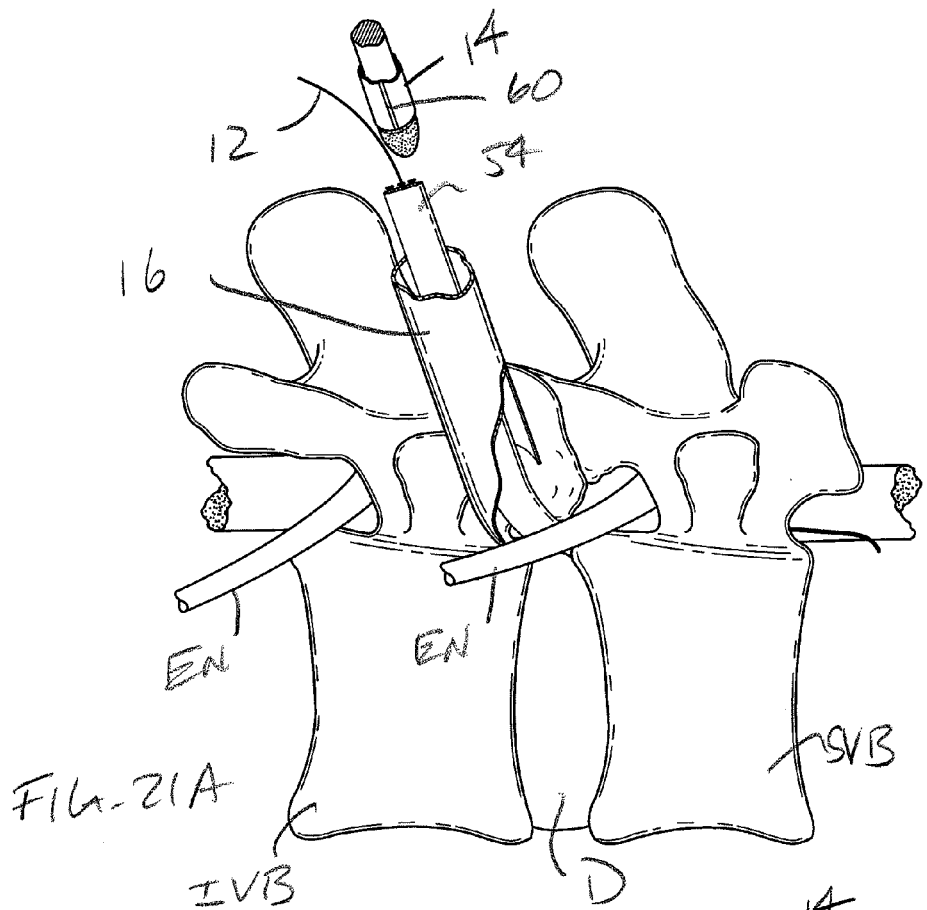
Figure 21B:
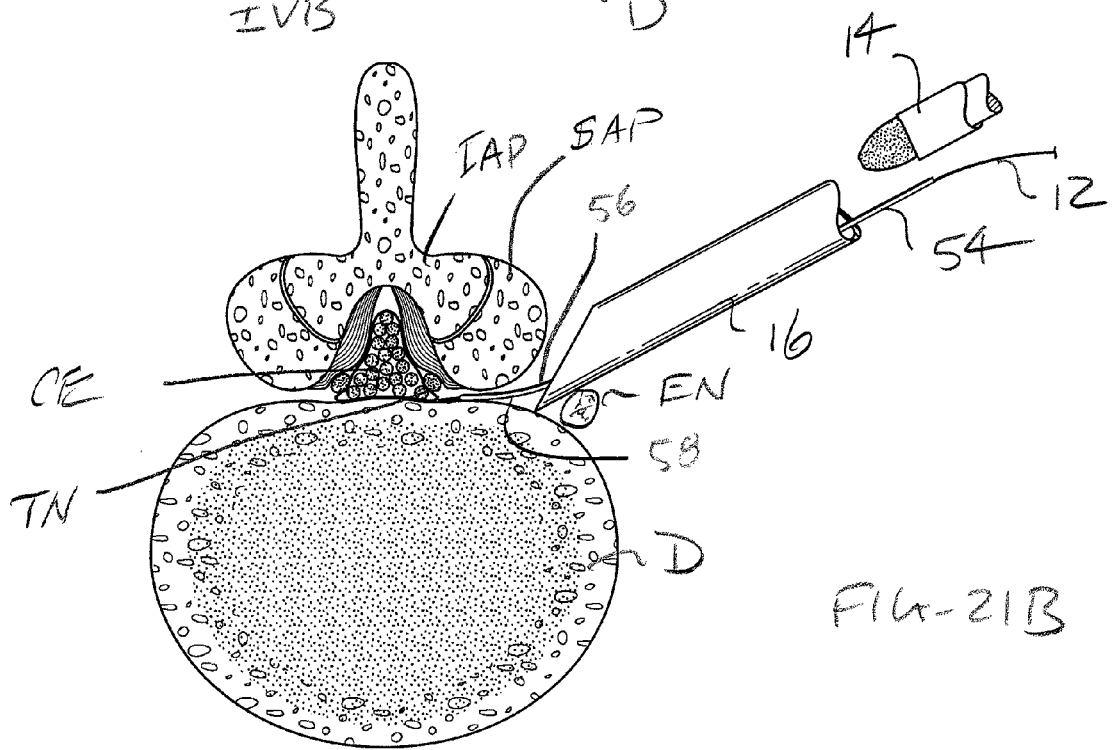
Figure 22A:
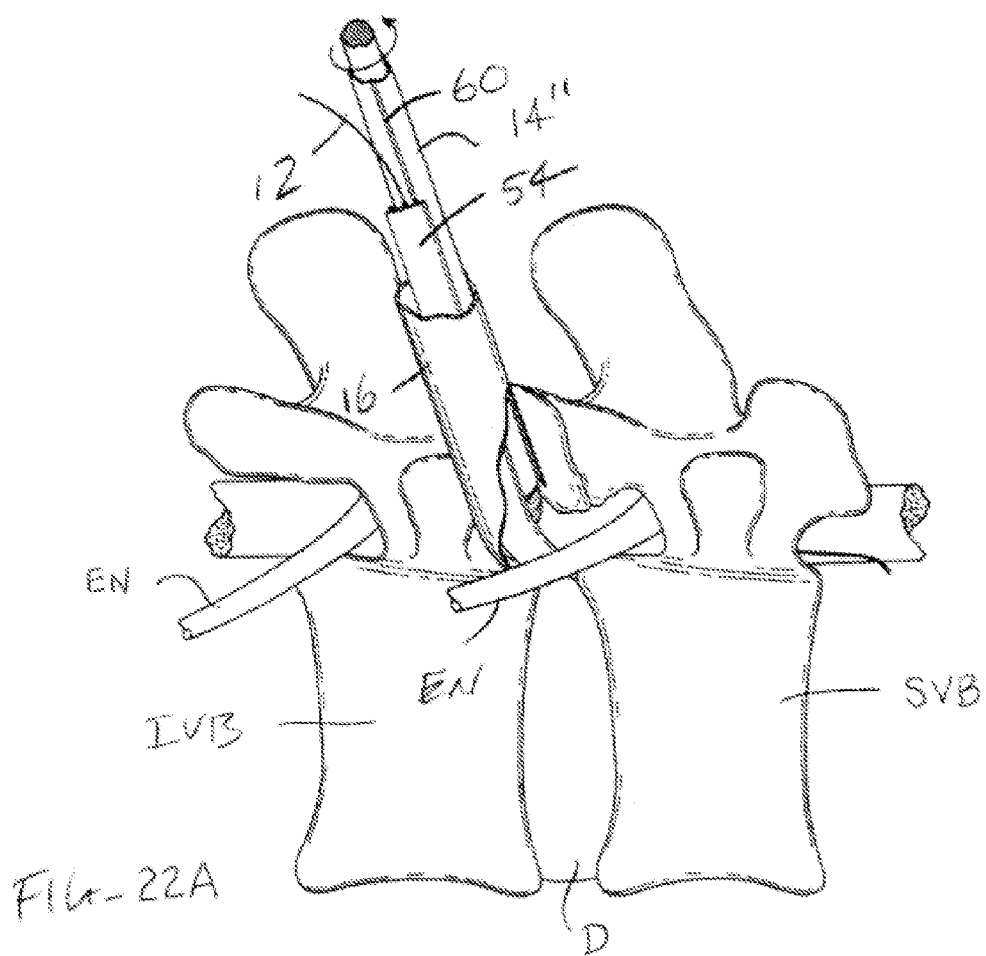
Figure 22B:
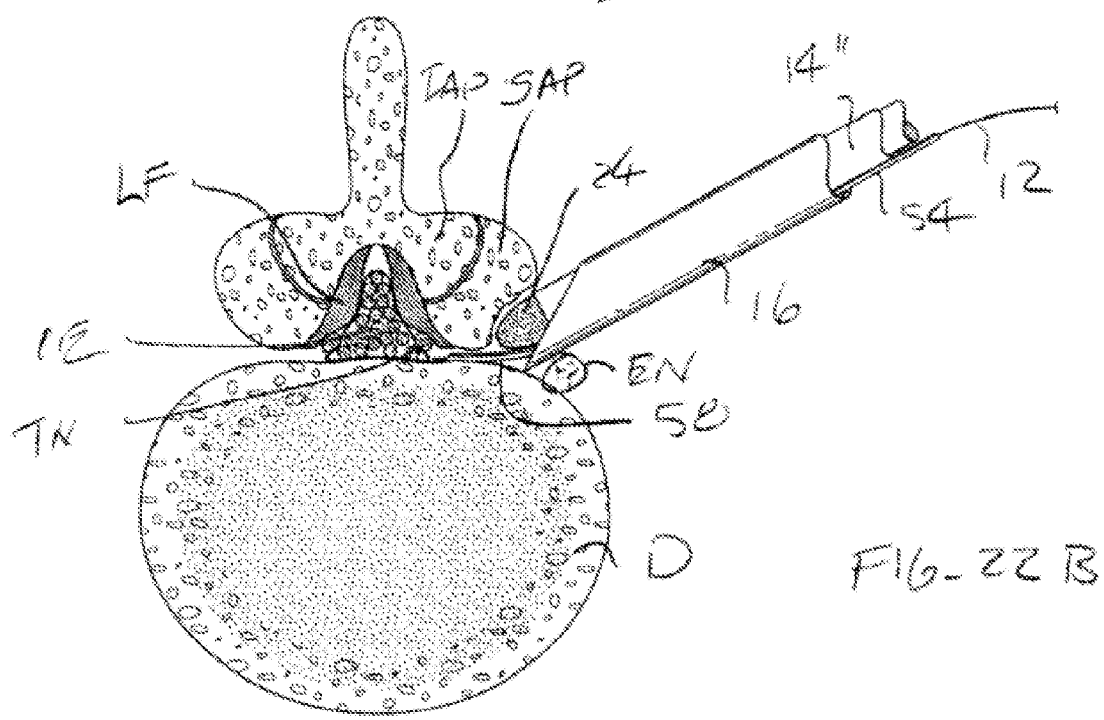

Referring now to FIGS. 20A/B through 22A/B, alternative views of the guide track 54 (FIGS. 4-7) for placing the bone removal tool 14 will be described. Placement of access sheath 16 to a region adjacent the anterior surface of the superior articular process SAP is accomplished in the same manner described above for the earlier protocol. Instead of placing two guidewires, however, only a single guidewire 12 need be advanced through the access sheath 16. It is shown to be advanced through the epidural space in a cephalad direction, but it would also be possible to advance it in the caudal direction. Once the guidewire is in place, guide track 54 having three rails 56 is advanced through the access sheath so that a posterior surface 58 of the guide track 54 engages the disk D, as best seen in FIGS. 21A/B. The cutting tool 14" having channel 60 is then advanced over a rail of the guide track 54, as illustrated in FIGS. 22A/B. A rotating burr 24 is then actuated and used to remove bone from the anterior surface AS of the superior articular process SAP, as best shown in FIG. 22B. After a first volume of bone is removed with the bone removal tool 14" placed over the first rail 56, the tool can then be withdrawn and placed over a second of the three rails and be used to remove further bone. The process will be repeated with the bone removal tool 14" being placed over the third of the rails 56 in order to remove still additional bone from a successive segment. The cutting tool 14" in guide track 54 may then be removed and the ligamentum flavum LF optionally cut as described above in the previous embodiment.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for laterally decompressing one or more spinal nerve(s) adjacent to a target facet joint in the lumbar spine of a patient, said method comprising:
   percutaneously positioning a tool guide through an access penetration to an anterior surface of the superior articular process of the facet joint, wherein percutaneously positioning comprises positioning a guide track having a base, the base having a width and a thickness, the width being wider than the thickness, the base having at least one rail on a posterior surface thereof, wherein the guide track is positioned with the base adjacent a disk so that the base protects the disk as a bone removal tool is advanced over the rail;
   advancing the bone removal tool over the tool guide through the access penetration, wherein the base of the guide track has two or more rails comprising at least a first and a second rail;
   wherein the step of advancing the bone removal tool includes:
      advancing the bone removal tool over the first rail to remove a first segment of bone;
      withdrawing the bone removal tool along the first rail; and
      advancing the bone removal tool over the second rail to remove a second segment of bone;
      wherein removing bone using the bone removal tool relieves pressure on the one or more spinal nerve(s).

2. A method as in claim 1, wherein pressure is relieved from at least one of an exiting nerve, a transversing nerve, and nerves of the cauda equina.

3. A method as in claim 1, further comprising expanding an anchor on the tool guide to hold it in place.

4. A method as in claim 1, wherein percutaneously positioning comprises positioning at least one guidewire through the access penetration, wherein the bone removal tool is advanced over the guidewire.

5. A method as in claim 4, further comprising repositioning the guidewire and advancing the bone removal tool over the repositioned guidewire to remove successive segments of bone.

6. A method as in claim 4, wherein percutaneously positioning comprises positioning at least two guidewires through the access penetration, wherein the bone removal tool is advanced sequentially over said guidewires to remove said successive segments of the bone.

7. A method as in claim 6, wherein a first guidewire is directed in a cephalad direction through an epidural space and a second guidewire is directed in a caudal direction through the epidural space, wherein the bone removal tool is advanced sequentially over the first and second guidewires to remove successive segments of the bone.

8. A method as in claim 1, further comprising repositioning the guide track and advancing the bone removal tool over the repositioned guide track to remove successive segments of bone.

9. A method as in claim 1, further comprising placing an access sheath through the access penetration wherein the tool guide is positioned in a passage of the sheath.

10. A method as in claim 9, wherein placing the access sheath comprises:
    percutaneously advancing a hollow needle to position a distal end of the needle at the target facet joint to create a percutaneous tract;
    positioning a sheath placement guidewire through the needle; removing the needle, leaving the sheath placement guidewire in place;

advancing one or more dilators over the sheath placement guidewire to enlarge the percutaneous tract;

positioning the access sheath over the sheath placement guidewire; and removing the sheath placement guidewire from the sheath and leaving the sheath in the dilated percutaneous tract.

11. A method as in claim 9, wherein the access sheath has an asymmetrically recessed end with a distally extending tip which is engaged against a disk adjacent the facet joint, wherein the distally extending tip protects the disk and exiting nerve root while the recess exposes articular surface for engagement by the bone removal tool.

12. A method as in claim 9, wherein the tool is advanced and retracted to reciprocate the rotating burr over the articular surface to remove impinging material.

13. A method as in claim 1, wherein removing bone comprises engaging a rotating burr on the bone removal tool against the anterior surface of the superior articular process.

14. A method as in claim 13, wherein the surface of the burr has a diameter from 3 mm to 10 mm and the burr is rotated at 25,000 to 125,000 rpm.

15. A method as in claim 13, further comprising delivering a cooling medium to the rotating burr to remove heat.

16. A method as in claim 13, further comprising replacing the burr with a larger burr to remove more bone.

17. A method as in claim 16, wherein a first burr having a diameter from 1 mm to 3 mm is used followed by successive burrs having larger diameters up to from 5 mm to 10 mm.

18. A method as in claim 1, wherein the burr is rotated in a single rotational direction.

19. A method as in claim 1, wherein the direction of rotation of the burr is periodically reversed.

20. A method as in claim 1, further comprising cutting the ligamentum flavum to further relieve pressure on the spinal nerve(s).

21. A method as in claim 20, wherein the ligamentum flavum is cut in a region which relieves pressure on a transversing spinal nerve.

22. A method as in claim 1, further comprising imaging the target facet joint and surrounding tissue while positioning and advancing the bone removal tool and removing bone with said tool.

23. A method as in claim 22, wherein imaging comprises fluoroscopy, computer tomography, or magnetic resonance imaging.

24. A method as in claim 22, wherein imaging comprises endoscopy with a scope positioned through the access penetration.

* * * * *